US012751837B2

(12) United States Patent
Riemhofer et al.

(10) Patent No.: US 12,751,837 B2
(45) Date of Patent: *Oct. 6, 2026

(54) INTERFIXATED VERTEBRAL BODY REPLACEMENT AND INSERTION METHODS

(71) Applicant: NuVasive, INC., San Diego, CA (US)

(72) Inventors: Byron Riemhofer, San Diego, CA (US); Thomas Sweeney, San Diego, CA (US); James Lee, San Diego, CA (US); Scott Lish, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 17 days.

This patent is subject to a terminal disclaimer.

(21) Appl. No.: 18/943,208

(22) Filed: Nov. 11, 2024

(65) Prior Publication Data

US 2025/0064602 A1 Feb. 27, 2025

Related U.S. Application Data

(63) Continuation of application No. 17/931,575, filed on Sep. 13, 2022, now Pat. No. 12,138,180, which is a continuation of application No. 16/995,602, filed on Aug. 17, 2020, now Pat. No. 11,517,451, which is a continuation of application No. 15/395,792, filed on Dec. 30, 2016, now Pat. No. 10,786,368.

(60) Provisional application No. 62/273,445, filed on Dec. 31, 2015, provisional application No. 62/273,443, filed on Dec. 31, 2015, provisional application No. 62/273,377, filed on Dec. 30, 2015.

(51) Int. Cl.

| | |
|---|---|
| ***A61F 2/46*** | (2006.01) |
| ***A61B 17/17*** | (2006.01) |
| ***A61B 17/88*** | (2006.01) |
| ***A61F 2/44*** | (2006.01) |
| *A61B 90/00* | (2016.01) |
| *A61F 2/30* | (2006.01) |

(52) U.S. Cl.

CPC ........ *A61F 2/4611* (2013.01); *A61B 17/1757* (2013.01); *A61B 17/8872* (2013.01); *A61B 17/8877* (2013.01); *A61B 17/8891* (2013.01); *A61F 2/4455* (2013.01); *A61B 2090/0812* (2016.02); *A61F 2002/30266* (2013.01); *A61F 2002/30787* (2013.01); *A61F 2002/30904* (2013.01); *A61F 2/4603* (2013.01); *A61F 2002/4627* (2013.01); *A61F 2002/4687* (2013.01)

(58) Field of Classification Search

CPC ............ A61B 17/8875; A61B 17/8877; A61B 17/888; A61B 17/8883; A61B 17/8886; A61B 17/8888; A61B 17/8891; A61B 17/7076; A61B 17/7082; A61F 2/4611; A61F 2002/449

See application file for complete search history.

(56) References Cited

U.S. PATENT DOCUMENTS 7,083,621 B2 * 8/2006 Shaolian ............ A61B 17/1757 606/259
7,580,743 B2 * 8/2009 Bourlion ................ A61B 5/053 606/80

(Continued)

*Primary Examiner* — Anu Ramana

(57) ABSTRACT

Implants and instruments for providing an ideal trajectory for the insertion of instruments and screws during implantation of an interbody implant in a spinal surgery are disclosed.

18 Claims, 21 Drawing Sheets

(56) References Cited

U.S. PATENT DOCUMENTS

| | | | | | |
|---|---|---|---|---|---|
| 7,722,623 | B2 * | 5/2010 | Franks | A61B 17/7091 606/104 |
| 8,231,635 | B2 * | 7/2012 | Sharifi-Mehr | A61B 17/7035 81/62 |
| 8,303,598 | B2 * | 11/2012 | Frankel | A61B 17/8875 606/92 |
| 8,366,719 | B2 * | 2/2013 | Markey | A61B 34/20 606/104 |
| 8,998,921 | B2 * | 4/2015 | Sharifi-Mehr | A61B 17/8605 606/86 A |
| 9,216,048 | B2 * | 12/2015 | Markey | A61B 17/1626 |
| 9,539,043 | B2 * | 1/2017 | DeFalco | A61B 17/8875 |
| 9,855,150 | B2 * | 1/2018 | Altarac | A61F 2/4455 |
| 10,512,547 | B2 * | 12/2019 | Altarac | A61F 2/4455 |
| 10,531,960 | B2 * | 1/2020 | McDonough | A61B 17/88 |
| 10,624,757 | B2 * | 4/2020 | Bost | A61F 2/4611 |
| 11,517,444 | B2 * | 12/2022 | McDonough | A61B 17/86 |
| 11,871,975 | B2 * | 1/2024 | Brown | A61B 17/1626 |
| 12,409,045 | B2 * | 9/2025 | Struck | A61F 2/442 |
| 12,458,422 | B2 * | 11/2025 | Brown | A61B 17/1626 |
| 2004/0255734 | A1 * | 12/2004 | Casutt | B25B 23/1427 81/467 |
| 2005/0119660 | A1 * | 6/2005 | Bourlion | A61B 17/1626 606/80 |
| 2005/0149036 | A1 * | 7/2005 | Varieur | A61B 17/7086 606/86 R |
| 2006/0111713 | A1 * | 5/2006 | Jackson | A61B 17/7037 606/279 |
| 2007/0016194 | A1 * | 1/2007 | Shaolian | A61B 17/7083 606/86 A |
| 2014/0277164 | A1 * | 9/2014 | Ramsay | A61B 17/7076 606/279 |
| 2017/0056199 | A1 * | 3/2017 | Altarac | A61F 2/447 |
| 2025/0064602 | A1 * | 2/2025 | Riemhofer | A61F 2/4611 |

* cited by examiner

INTERFIXATED VERTEBRAL BODY REPLACEMENT AND INSERTION METHODS

CROSS-REFERENCE TO RELATED APPLICATIONS

This application is a continuation of U.S. patent application Ser. No. 17/931,575, now U.S. Pat. No. 12,138,180 filed on Sep. 13, 2022, which is a continuation of U.S. patent application Ser. No. 16/995,602, now U.S. Pat. No. 11,517,451 filed on Aug. 17, 2020, which is a continuation of U.S. patent application Ser. No. 15/395,792 filed on Dec. 30, 2016, now U.S. Pat. No. 10,786,368, which claims priority to U.S. provisional application No. 62/273,377, filed on Dec. 30, 2015, U.S. provisional application No. 62/273,445, filed on Dec. 31, 2015, and U.S. provisional application No. 62/273,443, filed on Dec. 31, 2015, the entire disclosures of which are incorporated herein by reference.

FIELD OF THE DISCLOSURE

The present disclosure relates generally to medical devices, more specifically spinal implants, implant insertion assemblies, implant insertion guides, and surgical methods for replacing at least a portion of one or more vertebral bodies of the spine.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the pelvic region of the vertebral column. These fused vertebrae consist of the sacral and coccygeal region of the vertebral column.

The main functions of the spine are to provide support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing).

Each year millions of people suffer from back pain arising from defects in the intervertebral disc space. Commonly, surgical interventions directed at promoting fusion across the affected joint are employed to permanently provide long term pain relief to the patient. Typically, such fusion surgeries involve performing a partial or complete discectomy to prepare the disc space, and then implanting a natural or synthetic intervertebral fusion implant within the prepared disc space.

SUMMARY

The present application describes implants and instruments for performing surgical procedures on the spine, including one or more for providing an ideal trajectory for the insertion of instruments and screws during implantation of an interbody implant.

According to one example, an insertion guide providing an ideal trajectory for placement of instruments during implantation of an interbody implant in a spinal surgery is described. The insertion guide has a central body, an inserter tab stop, and one or more cylindrical guide tubes. There is an aperture through the central body for interaction with an insertion tool. The inserter stop extends from the trailing end of the insertion guide to interact with an insertion tool. The guide tubes are generally cylindrical with a lumen and are set at fixed angles that correspond with the angles of the screw holes in an interbody implant.

According to another aspect, the insertion guide may have an engagement mechanism on the inserter stop tab that allows a secure and reversible interconnection of the guide with an insertion tool.

According to another aspect, the insertion guide may have a geometrically shaped edge at the trailing end of the guide tubes to provide secure engagement with an insertion tool. According to another aspect, the geometric edge may have crenellations.

According to another aspect, the insertion guide may be made of a radiolucent material. According to another aspect, the insertion guide may be made of aluminum which is both radiolucent and light weight.

According to another aspect, the insertion guide may have between one and four guide tubes according to the surgical need. In some aspects, the insertion guide has one guide tube. In another aspect, the insertion guide has three tubes.

According to a second example, an insertion instrument that provides an ideal trajectory for placement of instruments during implantation of an interbody implant is described. The insertion instrument comprises an elongate tubular element, thumbwheel, and an insertion head. The insertion head has one fixed arm and one pivoting arm. The tubular element has an internal draw rod with a threaded portion that interacts with a threaded portion of the lumen of the thumbwheel. Rotation of the thumbwheel results in movement of the internal draw rod which in turn moves the pivoting arm. Connected to the upper surface of the insertion head is an insertion guide tube positioned at an appropriate angle to align with a screw hole on the interbody implant.

According to another aspect, the insertion instrument has an adjustable insertion guide tube attached to the insertion head at a pivoting joint. The pivoting guide tube has a fixed guide post attachment to allow repositioning. The guide post is sized to slide within an aperture through the insertion head. The position of the guide tube may be fixed by insertion of a set screw which contacts the guide post and prevents movement.

According to a third example a driver for insertion of bone screws during spinal surgery is described. The driver comprises a central shaft with two rotation grips located at the proximal end and a driver tip and hexabit driver located at the distal end. The driver tip engages the screw, and the hexabit driver engages the set screw. The first rotation grip rotates the driver tip to set the screw. The second rotation grip rotates the hexabit driver to set the set screw. The driver also includes an indicator that the screw is properly seated. When the screw is properly set, the driver provides one or more indicators that may be visual, audible, or tactile.

According to another aspect, the driver may have a driver tip that moves relative to the shaft of the driver. As the screw is set, the driver tip moves. The indicator may be a colored band that is covered by the driver tip when the screw is properly seated.

According to another aspect, the driver may include a sleeve located near the driver tip. The sleeve rotates and moves relative to the driver. Beneath the sleeve are a button, internal spline, and a spring. The spline is composed of a series of lengthwise grooves arranged around the outer surface of the driver near the driver tip. The spring is wound around the spline. When a screw is inserted, the sleeve moves and compresses the spring. When the screw is properly set, the button pops to give an audible and visual indicator giving a tactile indicator that the screw is properly set. A spline pin may interact with the spline to prevent additional rotation, giving a tactile indicator that the screw is properly set.

According to a fourth example, a system for insertion of a bone screw at an ideal trajectory during spinal surgery is described. The system comprises an interbody implant, an insertion guide, an insertion instrument, and a driver. The interbody implant has one or more screw holes and one or more holes for an insertion instrument. The insertion guide has one or more guide tubes aligned with the screw holes of the interbody implant, and has one or more holes for an insertion instrument. The insertion instrument has one or more arms that are sized to pass through the holes of the guide and the interbody implant to reversibly connect all three pieces together. The driver tip is sized to pass through the guide tubes and the screw holes to the desired site for insertion of the screws.

According to a fifth example, an insertion instrument for placement of instruments during implantation of an interbody implant is described. The insertion instrument comprises a hollow elongate tubular element with a thumbwheel and an insertion head at opposite ends. The thumbwheel is generally cylindrical with a threaded lumen. There is an inner shaft within the bore of the tubular element. The inner shaft has a threaded portion that engages with the threaded portion of the lumen of the thumbwheel so that rotation of the thumbwheel results in movement of the inner shaft. The insertion head has one or more insertion arms that project forward and that are sized to pass through corresponding insertion holes on a guide and an interbody implant to reversibly connect the insertion instrument to the guide and the interbody implant. The lower surface of the insertion head includes a keyed mechanism to interlock with a complementary feature on the insertion guide.

According to a sixth example, an interbody implant for insertion of a bone screw at an ideal trajectory during spinal surgery s described. The interbody comprises a top surface, a bottom surface, two opposing side walls, a leading end, and a trailing end. The top and bottom surfaces include anti-migration features. One or more screw holes extend through the implant at an angle from the trailing end to the top or bottom surface. The screw holes have an interior spherical surface that interacts with a fully seated screw. The implant includes one or more insertion holes through the trailing end. The implant also includes one or more insertion recesses on the opposing side wall for interaction with an insertion instrument.

BRIEF DESCRIPTION OF THE DRAWINGS

FIG. 1A shows a perspective view. FIG. 1B shows a sectional view. FIG. 1C shows a rear view. FIG. 1D shows a side view.

FIG. 16A shows a top view. FIG. 16B shows a sectional view.

FIG. 16C shows a top view of the insertion head of the instrument.

FIG. 17A shows a top view. FIG. 17B shows a sectional view.

FIG. 17C shows a top view of the insertion head of the instrument.

FIG. 19A shows a side view. FIG. 19B shows a sectional view. The set screw is in the loosened position.

DETAILED DESCRIPTION

Figure 1A:
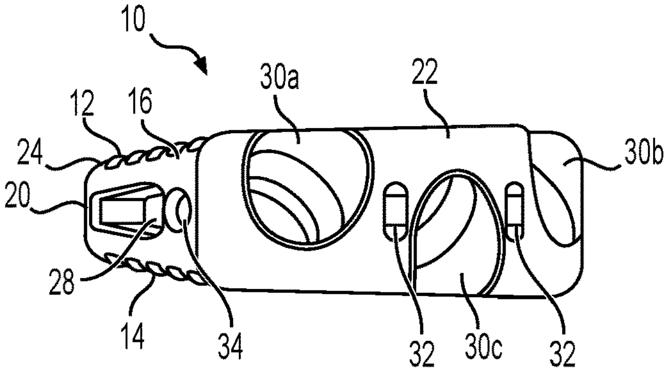
FIGS. 1A-1D show alternative views of an interfixated interbody implant according to one embodiment.
Figure 1B:
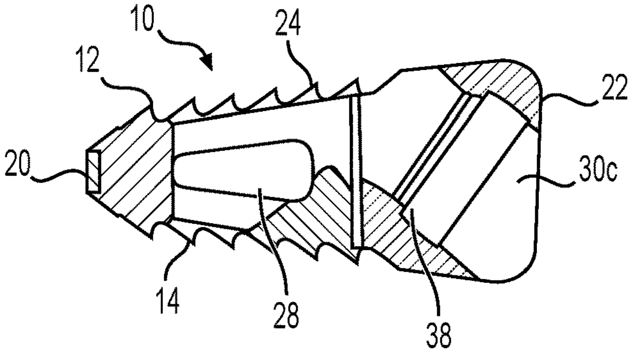

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The implants, inserters and guides disclosed herein boasts a variety of inventive features and components that warrant patent protection, both individually and in combination.

With respect to FIG. 1, several views of an exemplary embodiment of an interfixated interbody implant are shown. The interbody implant 10 may be constructed of any suitable non-bone composition, including but not limited to polymer compositions (e.g. poly-ether-ether-ketone (PEEK) and/or poly-ether-ketone-ketone (PEKK)), ceramic, metal and/or any combination of polymer compositions, ceramic and metal. The spinal fusion implant may be provided with a surface coating (for example, titanium plasma spray) to encourage bone growth onto endplate contacting surfaces. The spinal fusion implant 10 of the present invention may be provided in any number of shapes and sizes depending upon the particular surgical procedure or need. By way of example only, the spinal fusion implant 10 may have a width ranging between 8 and 14 mm, a height ranging between 6 and 18 mm, and a length ranging between 20 and 45 mm.

The interbody implant 10 of the present invention includes a top surface 12, a bottom surface 14, opposing first and second lateral side walls 16, 18, a leading end 20 and an opposing trailing end 22. The spinal fusion implant 10 of the present invention may be used to provide temporary or permanent fixation within an orthopedic target site. To do so, the spinal fusion implant 10 may be introduced into a disc space while locked to a surgical insertion instrument and thereafter employed in the proper orientation and released. Once deposited in the disc space, the spinal fusion implant 10 of the present invention effects spinal fusion over time as the natural healing process integrates and binds the implant.

The top and bottom surfaces 12, 14 are configured to engage the vertebral bodies adjoining the target disc space. Accordingly, the top and bottom surfaces 12, 14 each preferably include a plurality of anti-migration features designed to increase the friction between the interbody implant 10 and the adjacent contacting surfaces of the vertebral bodies. Such anti-migration features may include ridges (or teeth) 24 provided along the top surface 12 and/or bottom surface 14. The friction prohibits migration of the implant 10 after insertion into the intervertebral space and during the propagation of natural bony fusion. It should be appreciated by one skilled in the art that such ridges (or teeth) 24 can be oriented in a particular direction which will stabilize the implant in several degrees of rotation during placement.

The interbody implant 10 of the present invention may also be provided with one or more radiographic markers to allow for visual determination of proper implant placement. The radiographic markers may be manufactured from any of a variety of suitable radiopaque materials, including but not limited to a metal, ceramic, and/or polymer material, preferably having radiopaque characteristics. The radiographic markers may be provided in any size or shape suitable to facilitate effective and accurate visualization of implant placement.

The interbody implant includes a large fusion aperture 26 extending in a vertical fashion between top and bottom surfaces 12, 14. The aperture may be provided in any number of suitable shapes, including but not limited to, generally circular, generally triangular, and/or generally oblong. This single aperture 26 is an additional feature for promoting fusion between the upper and lower vertebral bodies which allows a bony bridge to form though the interbody implant 10.

According to another further aspect of the present invention, this fusion may be facilitated or augmented by including osteoinductive material(s) within the aperture 26 and/or adjacent to the spinal fusion implant 10. Such osteoinductive materials may be introduced before, during, or after insertion of the spinal fusion implant 10 of the present invention, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions.

First and second lateral side walls 16, 18 are generally parallel to one another. The spinal fusion implant 10 may be further provided with one or more lateral apertures 28 extending generally perpendicularly therethrough from one lateral side 16 to the other 18, as shown in FIG. 1D. The lateral apertures 28 function to provide visualization at the time of implantation and at subsequent clinical evaluations. The lateral apertures 28 may be provided in any of a variety of suitable shapes, including but not limited to generally circular, generally triangular, generally rectangular, and/or generally oblong, or any combination thereof. Although the interbody implant 10 herein includes a pair of lateral apertures 28, the spinal fusion implant 10 may include any number of lateral apertures 28 as desired.

Based on the generally radiolucent nature of the implant 10, the lateral apertures 36 provide the ability to visualize the interior of the implant 10 during X-ray and/or other suitable imaging techniques which are undertaken from the lateral (or "side") perspective of the implant 10. If fusion has taken place, the lateral apertures 28 will provide a method for the surgeon to make follow up assessments as to the degree of fusion without any visual interference from the spinal fusion implant 10. Further, the lateral apertures 28 will provide an avenue for cellular migration to the exterior of the spinal fusion implant 10. Thus the spinal fusion implant 10 will serve as additional scaffolding for bone fusion on the exterior of the spinal fusion implant 10.

The interbody implant 10 further includes one or more screw holes 30 angled to allow screws to pass through the holes and when fully seated, engage the vertebral bodies adjoining the target disc space to secure the implant 10 in position. In the exemplary embodiment shown in FIG. 1, the interbody implant has three screw holes 30 *a*, 30 *b*, 30 *c*, as shown most clearly in FIG. 1C. Two screw holes 30 *a*, 30 *b* located proximal to each of the lateral side walls 16, 18 are oriented at an angle extending from the trailing end 22 to the bottom surface 14. A medial screw hole 30 *c* is located equidistant from the two lateral side walls 16, 18 and is oriented at an angle extending from the trailing end 22 to the top surface 12. It will be appreciated that other embodiments may have alternative arrangement and number of screw holes depending upon the needs of a given surgical procedure. As shown most clearly in the sectional view of FIG. 1B, the screw holes 30 of the implant 10 may include an internal spherical surface 38. As described more fully below, the spherical surface may interact with the head of a bone screw 618 and provide feedback when the screw is fully seated.

Figure 1C:
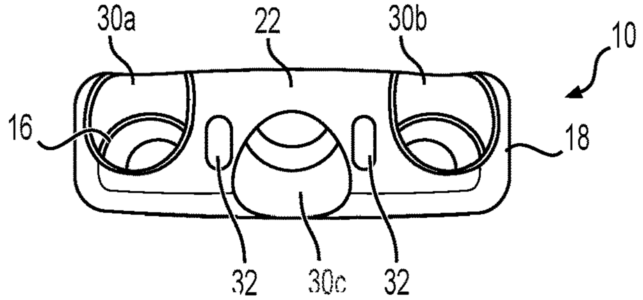
Figure 1D:
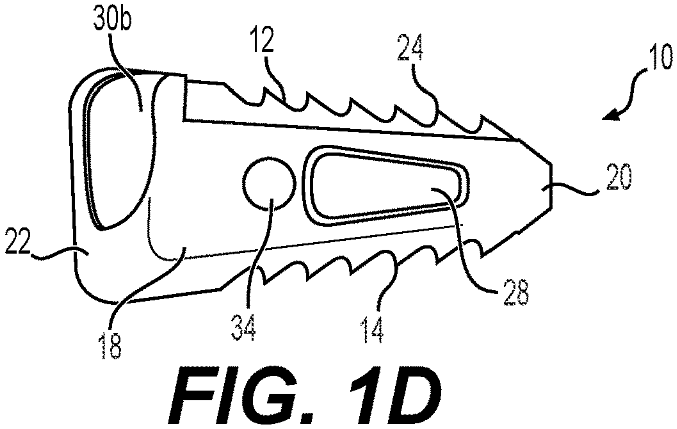

As shown in FIGS. 1A and 1C, the interbody implant 10 further includes one or more insertion apertures 32 which extend inwardly in a generally perpendicular fashion relative to the trailing end 22. In the exemplary embodiment shown, which is appropriate for an anterior approach, two insertion apertures 32 flank the medial screw hole 30 *c*. The insertion apertures 32 may be provided having any number of suitable shapes or cross-sections, including but not limited to circular or triangular. Insertion apertures 32 are dimensioned to receive and engage with an insertion instrument during insertion as will be described in greater detail below. The location of the insertion aperture 32 will vary in alternative embodiments where the implant is intended for use in an anterolateral, lateral, posterior, or posterolateral approach. Such modifications may be made without departing from the scope of the invention and are within the knowledge of a person of ordinary skill in the art.

As shown in FIG. 1D, the interbody implant 10 may further include lateral engagement recesses 34 which extend inwardly in a generally perpendicular fashion relative to the first and second lateral sides 16, 18. The lateral engagement recess 34 may be provided having any number of suitable shapes or cross-sections, including but not limited to circular or triangular. Furthermore, the lateral engagement recess 34 may extend fully or at least partially along the length of the lateral side walls 16, 18. Lateral engagement recess 34 is dimensioned to receive and engage with an insertion instrument (described below) to provide steerability and torsional support during insertion as will be described in greater detail below.

With respect to FIGS. 2-6, an exemplary embodiment of an insertion guide 1 according to one embodiment is shown. The guide 100 facilitates insertion of screws through an interbody implant 10 by providing the ideal trajectory for an awl, drill, tap, screw, or other tool. As will be described further below, the guide 100 may also interact with the driver 600 to provide feedback during insertion of the screws. It will be appreciated that the guide 100 is suitable for use in cervical, thoracic, and lumbar applications. It may be used from an anterior, anterolateral, lateral, posterior, or posterolateral approach without departing from the scope of the invention. Although the guide may be made of any suitable bio-compatible material, the use of a radiolucent material, such as anodized aluminum allows fluoroscopic visualization of the surgical site without the guide 100 blocking the surgeon's view of anatomical features and other tools. Use of anodized aluminum also reduces the weight of the guide 100. In some embodiments, the guide 100 may be color-coded to provide a visual indication to the surgical team as to which guide 100 corresponds to the interbody implant 10 used in the surgery.

The guide 100 comprises a central body 102 with an upper surface 104, lower surface 106, first lateral side 108, second lateral side 110, a distal end 112, and a proximal end 114. The exemplary guide 100 shown in FIGS. 2-6 includes three guide tubes 118 *a*, 118 *b*, 118 *c* dimensioned to align with the screw holes 30 *a*, 30 *b*, 30 *c* of the interbody implant 10. The guide tubes 118 are generally cylindrical with a lumen 124 extending from a leading edge 120 aligned with the distal end 112 of the guide 100 to a trailing edge 122 of the guide tube 118.

In the exemplary embodiment, two lateral guide tubes 118 *a*, 118 *b* are located adjacent to the lateral sides of the guide 108, 110 and are arranged at a downward angle with the same degree of tilt as the lateral screw holes 30 *a*, 30*b* of the interbody implant 10. The medial guide tube 118*c* is located equidistant from the lateral sides 108, 110, and is arranged at an upward angle with the same degree of tilt as the medial screw hole 30*c* of the interbody implant 10. The guide tubes 118*a*, 118*b*, 118*c* each terminate in a leading edge 120 that is flush with the distal end 112 of the guide body 102. The leading edge 120 of the guide tubes 118*a*, 118*b*, 118*c* interacts with the trailing edge 36 of the screw holes 30*a*, 30*b*, 30*c* of the interbody implant 10. When the guide 100 is properly aligned with the implant 10, the leading edge 120 of each guide tube 118*a*, 118*b*, 118*c* corresponds to the trailing edge 36 of the screw holes 30*a*, 30*b*, 30*c* of the interbody implant and the screw holes 30*a*, 30*b*, 30*c* and guide tubes 118*a*, 118*b*, 118*c* are aligned in a linear fashion. The trailing edge 122 of the guide tubes 118*a*, 118*b*, 118*c* may include crenellations 138 that interlock with corresponding crenellations 640 on the driver 600 as described below. Alternatively, the trailing edge 122 of the guide tubes may end in an alternative geometric surface that may interact with the driver in a keyed mechanism. In some embodiments, the trailing edge 122 of the guide tubes 118 may end in a flat surface.

The guide 100 may further include one or more insertion apertures for engagement with an insertion instrument. In one exemplary embodiment, the guide 100 includes two insertion apertures 116 which extend through the guide body 102 from the distal end 112 to the proximal end 114 in a generally perpendicular fashion relative to ends 112, 114 of the guide 100. The insertion apertures 116 are arranged on either side of the medial guide tube 118C. The insertion apertures 116 may be provided having any number of suitable shapes or cross-sections, including but not limited to circular or triangular. Insertion apertures 116 are dimensioned to receive and engage with an insertion instrument (described below) during insertion as will be described in greater detail below.

In some embodiments, guide 100 includes an inserter stop 126 that extends as a tab-like projection from the proximal end 114 of the guide body 102. The inserter stop 126 has an upper 128 and lower 130 surface. In some embodiments, the upper surface 128 of the inserter stop may be aligned in generally the same plane as the upper surface 104 of the guide body 102. The inserter stop 126 projects from the proximal end 114 of the guide at the midpoint of the inserter body 102, equidistant from the lateral sides 108, 110 in a generally perpendicular fashion relative to the proximal end 114. The inserter stop 126 may include an engagement mechanism for securing the guide 100 to the insertion instrument 300. The engagement mechanism may be a spring plunger 132 to allow quick connection of the guide 100 to the insertion instrument 300. The ball element 134 of the spring plunger projects below the lower surface 130 of the inserter stop 126 and a spring housing 136 projects above the inserter stop 126. In other embodiments, the engagement mechanism may be a keyed tab which projects from the lower surface 130 of the inserter stop interacts with a corresponding slot on the insertion instrument 300. In other embodiments, the spring plunger or keyed tab is located on the insertion instrument 300 and interacts with a corresponding recess on the guide (100).

In an alternative embodiment shown in FIGS. 7-11, the guide 200 includes only one guide tube 202. The one-tube embodiment is essentially as described above for the three-guide tube embodiments. However, the lateral guide tubes 118*a*, 118*b* are absent. As shown most clearly in FIGS. 9 and 10, a single guide tube results in a narrower device which allows the surgeon to visualize the anatomy that is blocked by the lateral guide tubes in the three-tube embodiment described above.

The guide 200 comprises a central body 202 with an upper surface 204, lower surface 206, first lateral side 208, second lateral side 210, a distal end 212, and a proximal end 214. The exemplary guide 200 shown in FIGS. 7-11 includes one guide tube 218 dimensioned to align with the medial screw hole 30*c* of the interbody implant 10. The guide tube 218 is generally cylindrical with a lumen 224 extending from a leading edge 220 aligned with the distal end 212 of the guide 200 to a trailing edge 222 of the guide tube 218.

The guide tube 218 is located equidistant from the lateral sides 208, 210, and is arranged at an upward angle with the same degree of tilt as the medial screw hole 30*c* of the interbody implant 10. The guide tube 218 terminates in a leading edge 220 that is flush with the distal end 212 of the guide body 202. The leading edge 220 of the guide tubes 218 interacts with the trailing edge 36 of the screw hole 30*c* of the interbody implant 10. When the guide 200 is properly aligned with the implant 10, the leading end 220 of the guide tube 218 corresponds to the trailing end 36 of the screw hole 30*c* of the interbody implant 10 and the screw hole 30*c* and guide tube 218 are aligned in a linear fashion. The trailing edge of the guide tube 218 may include crenellations that interlock with corresponding crenellations on the driver 60 as described below. Alternatively, the trailing edge 222 of the guide tubes may end in an alternative geometric shape that may interact with the driver in a keyed mechanism. In some embodiments, the trailing edge of the guide tubes may end in a flat surface.

The guide 200 further includes two insertion apertures 216 which extend through the guide body 202 from the distal end 212 to the proximal end 214 in a generally perpendicular fashion relative to ends 212, 214 of the guide 200. The insertion apertures 216 are arranged on either side of the guide tube 218. The insertion apertures 216 may be provided having any number of suitable shapes or cross-sections, including but not limited to circular or triangular. Insertion apertures 216 are dimensioned to receive and engage with an insertion instrument (described below) during insertion as will be described in greater detail below.

The guide 200 includes an inserter stop 226 that extends as a tab-like projection from the proximal end 214 of the guide body 202. The inserter stop 226 has an upper 228 and lower 230 surface. The upper surface 228 of the inserter stop is generally aligned in the same plane as the upper surface 204 of the guide body 202. The inserter stop 226 projects from the proximal end of the guide at the midpoint of the inserter body 202, equidistant from the lateral sides 208, 210 in a generally perpendicular fashion relative to the proximal end 214. The inserter stop 226 includes an engagement mechanism for securing the guide 200 to the insertion instrument 300. The engagement mechanism may be a spring plunger 232 to allow quick connection of the guide 200 to the insertion instrument 300. The ball element 234 of the spring plunger projects below the lower surface 230 of the inserter stop 226 and a spring housing 236 projects above the inserter stop 226. In other embodiments the engagement mechanism may be a keyed tab which projects from the lower surface 230 of the inserter stop interacts with a corresponding slot on the insertion instrument 300.

It will be appreciated that alternative embodiments with two or four guide tubes are within the scope of this disclosure. The implant used in the surgical procedure, the surgical exposure, and the preferences of the surgeon will determine which guide is most appropriate for a given surgery.

It will be understood that the guides described in the present disclosure may be modified to suit a specific surgical approach such as anterior, posterior, lateral, anterolateral, or posterolateral, or may be used in open or minimally invasive procedures. Such variations are encompassed by this disclosure and are within the skills of a person of ordinary skill.

The interbody implant 10 may be introduced into a spinal target site though use of any variety of suitable surgical instruments having the capability to engage the implant. With respect to FIGS. 12-15, several views of an exemplary embodiment of an insertion instrument 300 are shown. According to a broad aspect, the insertion instrument includes a proximal region 302, a distal region 304, and elongate tubular element 306, and an inner shaft 308.

The elongate tubular element 306 is comprised of a proximal end 310, a distal end 312, and an inner bore 314 extending between proximal and distal ends 310, 312. At or near the proximal end 310 is a thumbwheel housing 316. At or near the distal end 312 is a pair of distal insertion members 318. The insertion members 318 are dimensioned to pass through the insertion apertures 116, 216 of the guide, and through the insertion apertures 32 of the implant 10. The insertion members 318 have a length adequate to pass through the guide 100, 200.

A handle (not shown) is in a fixed relationship with the elongate tubular element 306. The handle may be aligned with the elongate tubular element 306, but may also be positioned offset from the tubular element 306. The handle is also in a fixed relationship with the thumbwheel housing 316 allowing easy handling by the user. By way of example, the thumbwheel housing 316 holds a thumbwheel 320, a set screw 322, and at least one spacer 324. The thumbwheel is generally cylindrical with a threaded lumen. Because the handle is fixed, the user has easy access to the thumbwheel 320 and can easily and stably turn the thumbwheel 320 relative to the thumbwheel housing 316. The user may then employ the thumbwheel 320 to rotate the inner shaft 308 thereby advancing and retracting the distal insertion arms 336 as described below.

The elongate tubular element 306 is generally cylindrical and of a length sufficient to allow the device to span from the surgical target site to a location sufficiently outside the patient's body so that the handle and thumbwheel housing 316 can be easily accessed by the user. The inner shaft 308 is sized and dimensioned to be disposed within the inner bore 314 of the elongate tubular element 306. The inner shaft 308 is comprised of a proximal end 328, a distal end 330, and threaded intermediate portion 332. The threaded portion 332 engages the thumbwheel 320 to advance and retract the inner shaft 308 within the elongate tubular element 306.

Figure 14:
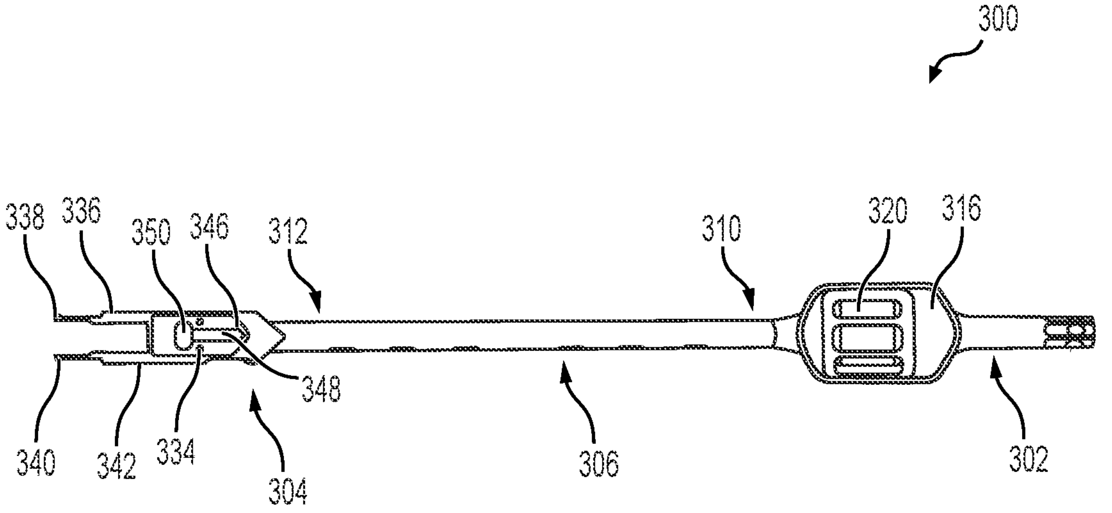
FIG. 14 shows a top view of the inserter of FIG. 13.
Figure 15:
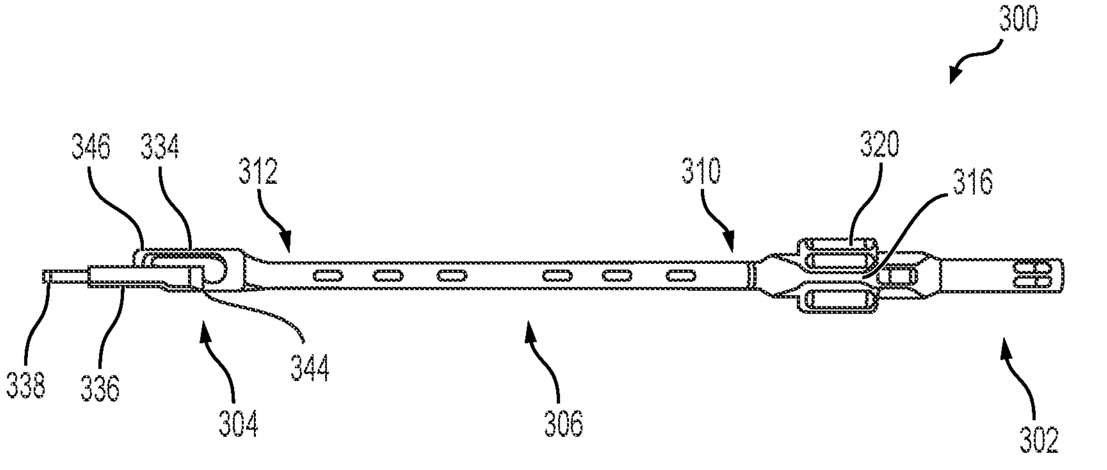
FIG. 15 shows a side view of the inserter of FIG. 13.

The distal end comprises a distal insertion head 334 and the insertion members 318. The insertion members 318 comprise a pair of insertion arms 336. The insertion arms 336 each have an outwardly facing engagement prongs 338 at the distal end 340. The proximal end 342 of the insertion arms 336 are longitudinally fixed to the inner shaft 308 such that rotation of the thumbwheel 320 advances and retracts the insertion arms 336. The insertion head has an upper face 344 and a lower face 346. As shown in FIG. 14, the lower face 346 comprises an engagement element 348 for interaction with the insertion guide 200, 300. In some embodiments, the engagement element 348 comprises a recess for receiving the ball element 134, 234 of the spring plunger 132, 232. In other embodiments, the engagement element 348 may be a keyed slot 350 as shown in FIG. 14, where the slot corresponds to a keyed tab projecting from the lower surface 130, 230 of the inserter stop 126, 226 of the insertion guide 100, 200. Alternative placement of the interlocking features on the guide and insertion instrument are possible. Such variations are within the knowledge of persons of skill in the art, and are encompassed by the present disclosure.

To prepare the implant 10 for insertion during a surgical procedure, the insertion arms 336 may be fully retracted by rotation of the thumbwheel 320. The insertion members 318 of the insertion instrument 300 are passed through the insertion apertures 116, 216 of the guide 100, 2. The insertion members 318 are passed into the insertion apertures 32 of the implant. The insertion arms 336 are sufficiently flexible that passage of the outwardly facing prongs 338 through the insertion apertures 32 of the implant exerts an inward force and compresses the insertion arms 336 inward sufficiently to allow the prongs 338 to pass through the aperture 32. The thumbwheel 320 is rotated to extend the insertion arms 336 until the outwardly facing engagement prongs 338 at the distal end 340 of the insertion arms pass completely through the trailing end 22 of the implant 10 and into the fusion aperture 26. Once the insertion arms 336 have been extended to the point that the engagement prongs 338 have passed fully through the insertion apertures 32, the inward pressure is released and the insertion arms 336 snap back into position and prevent the implant 10 from disengaging from the insertion instrument 300 during the insertion process. The thumbwheel 320 may be locked in position to prevent further rotation and extension of the insertion arms 336.

In surgical procedures where access to the surgical site is more limited, such as when an anterolateral approach is used, it may be preferable to have an insertion instrument with an integral guide tube to eliminate the bulkiness that would come from the use of two separate instruments as described above. FIGS. 16-27 show views of an exemplary embodiment of an insertion instrument with an adjustable guide tube.

The anterolateral interbody insertion instrument is designed to insert an interbody between two adjacent vertebral bodies. The instrument may be used to insert an interbody implant and place fixation devices at a particular trajectory. The instrument removes the need for a separate guide attached to the inserter and fulfills the surgical requirements with a single instrument. The mechanism for attachment to the interbody is similar to a standard insertion device, but the instrument also includes an adjustable guide tube for use in pilot hole preparation and screw placement. The method of using the inserter includes: attaching the inserter to an interbody of choice, loosening the adjustable guide tube, aligning the guide tube with the interbody screw hole, locking the guide tube in the desired position, and inserting the interbody and screw according to standard surgical technique.

According to a broad aspect, the insertion instrument 4 includes a proximal region 402, a distal region 404, and elongate tubular element 406, and an internal draw rod 408.

The elongate tubular element 406 is comprised of a proximal end 410, a distal end 412, and an inner bore 414 extending between proximal and distal ends 412, 414. At or near the proximal end 410 is a thumbwheel housing 416. A handle (not shown) is in a fixed relationship with the elongate tubular element 406 and the thumbwheel housing 416. In some embodiments the thumbwheel housing 416 holds a thumbwheel 420, a set screw 422, and at least one spacer 424. The thumbwheel is generally cylindrical with a threaded lumen. At or near the distal region 404 of the inserter is an insertion head 434 with a medial insertion arm 418 and a lateral insertion arm 426. The medial insertion arm 418, is in a fixed position and is dimensioned to pass through one of the medial insertion apertures 32 on the trailing end of the implant 10. The lateral insertion arm 426 is connected to the internal draw rod 408 at a pivot point 452 such that rotation of the thumbwheel 420 translates the internal draw rod 408 thereby pivoting the lateral insertion arm 426 as described below.

The elongate tubular element 406 is generally cylindrical and of a length sufficient to allow the device to span from the surgical target site to a location sufficiently outside the patient's body so that the handle and thumbwheel housing 416 can be easily accessed by the user. The internal draw rod 408 is sized and dimensioned to be disposed within the inner bore 414 of the elongate tubular element 406. The internal draw rod 408 is comprised of a proximal end 428, a distal end 430 and threaded intermediate portion 432. The threaded portion 432 engages the thumbwheel 420 to advance and retract the internal draw rod 408 within the elongate tubular element 406.

Figure 16A:
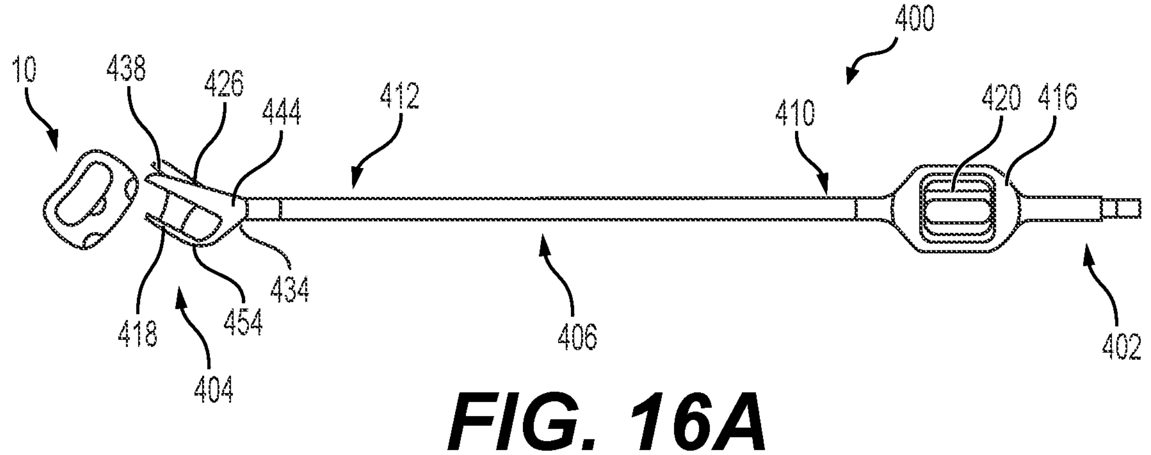
FIGS. 16A-16C show alternative views of an implant and a guide tube insertion instrument in the open position.
Figure 16B:
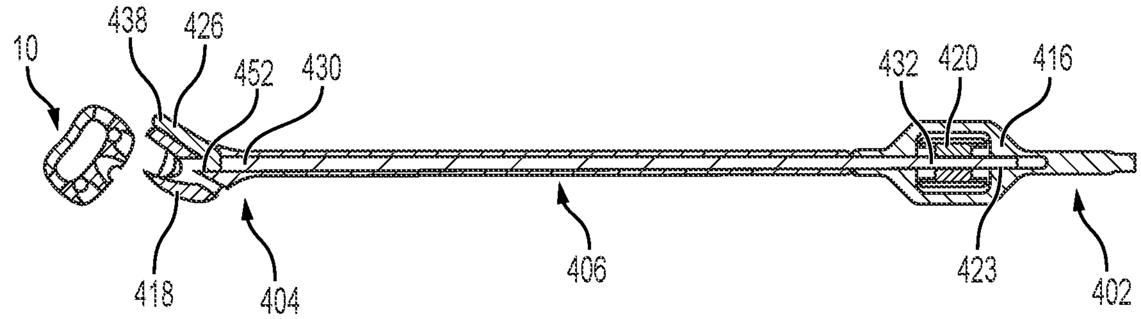
Figure 16C:
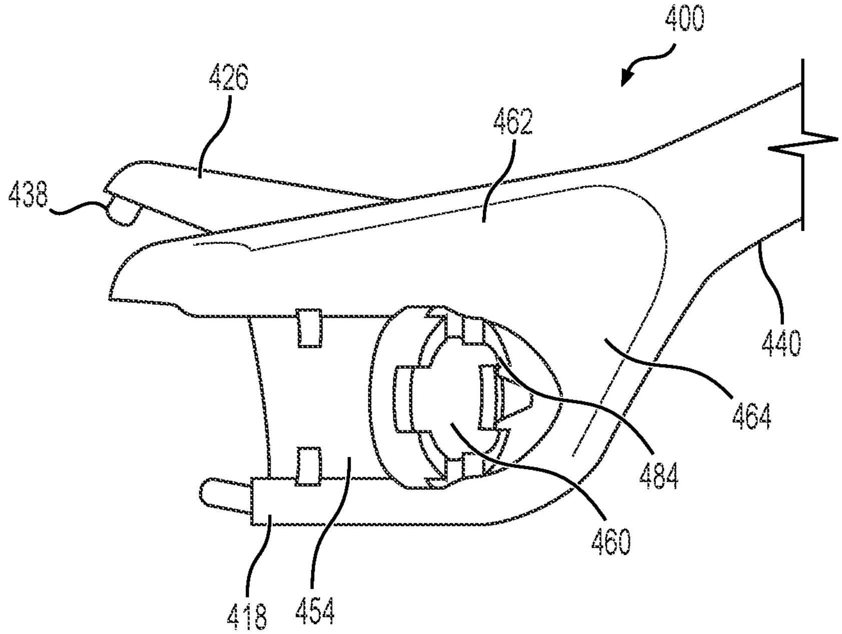
Figure 17A:
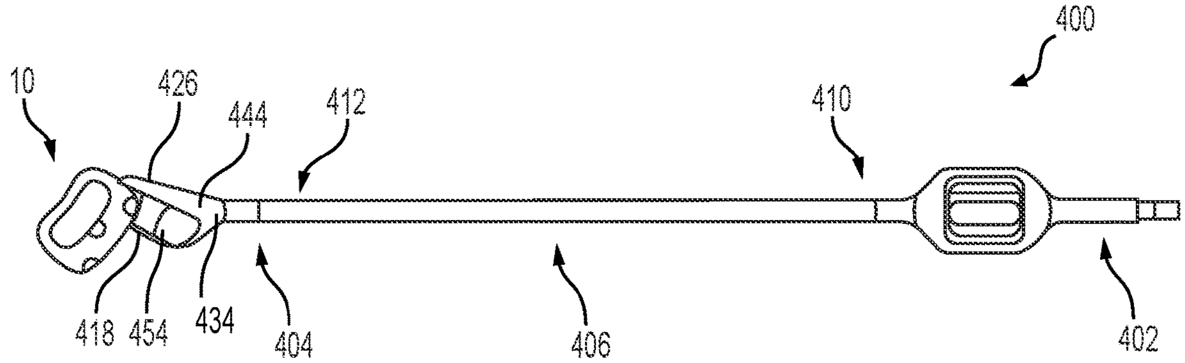
FIGS. 17A-17C show alternative views of an implant and a guide tube insertion instrument in the closed position.
Figure 17B:
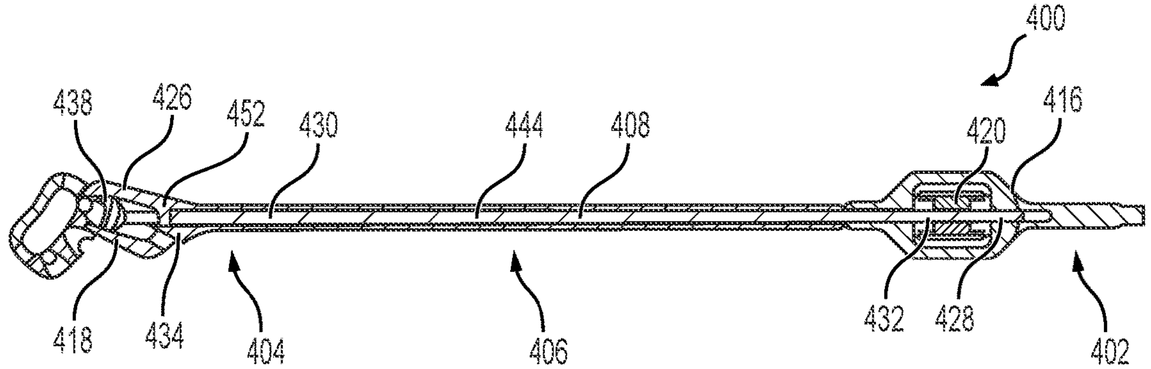
Figure 17C:
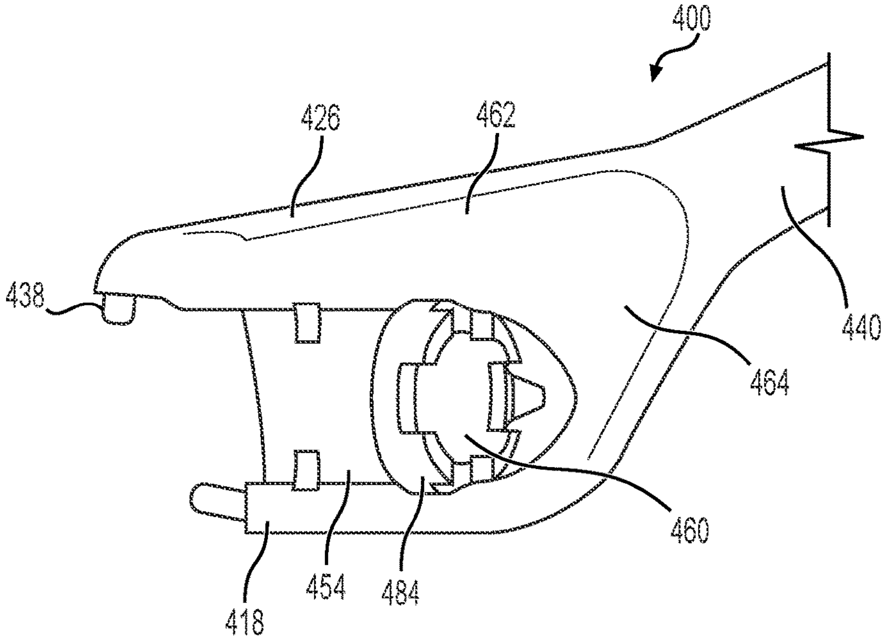
Figure 18:
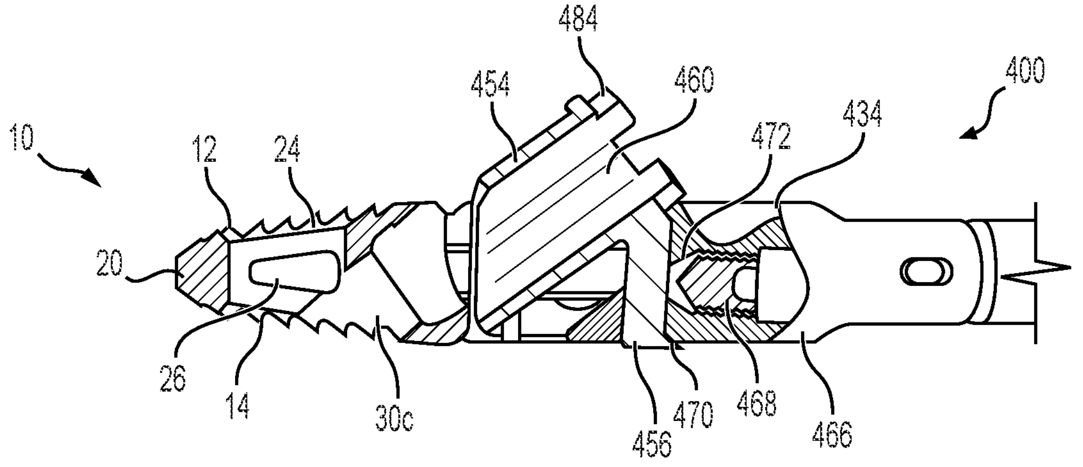
FIG. 18 shows a sectional view of a guide tube insertion instrument in association with an implant. The guide tube of the insertion instrument and the screw hole of the implant are misaligned. The set screw is in the loosened position.
Figure 19A:
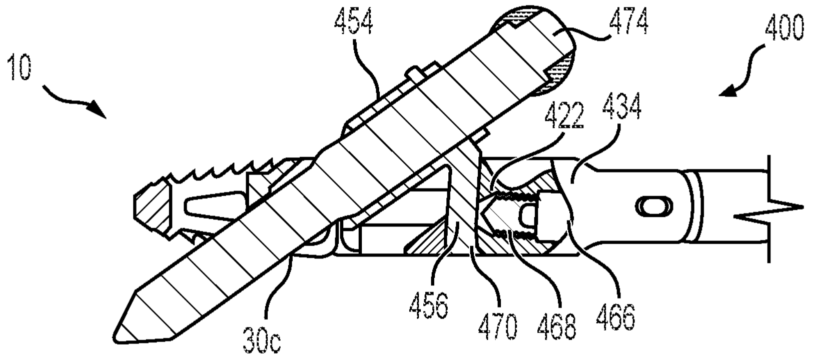
FIGS. 19A-19B show alternative views of the of the guide tube insertion instrument of FIG. 18 with an alignment tool. The tool aligns the guide tube of the insertion instrument and the screw hole of the implant.
Figure 19B:
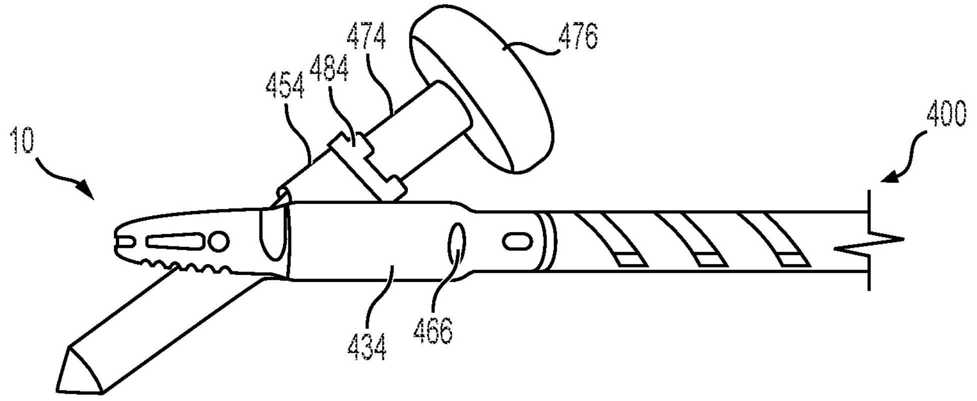
Figure 20:
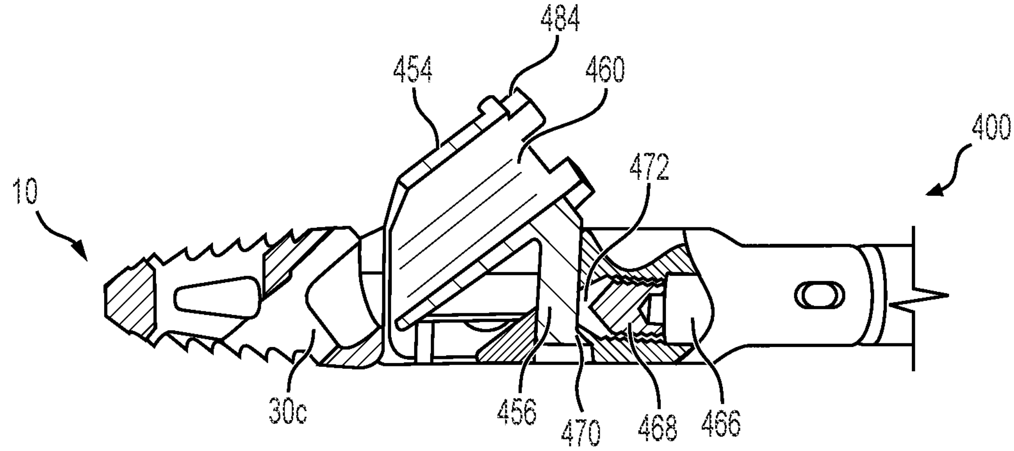
FIG. 20 shows a sectional view of a guide tube insertion instrument in association with an implant. The guide tube of the insertion instrument and the screw hole of the implant are aligned. The set screw is in the loosened position.
Figure 21:
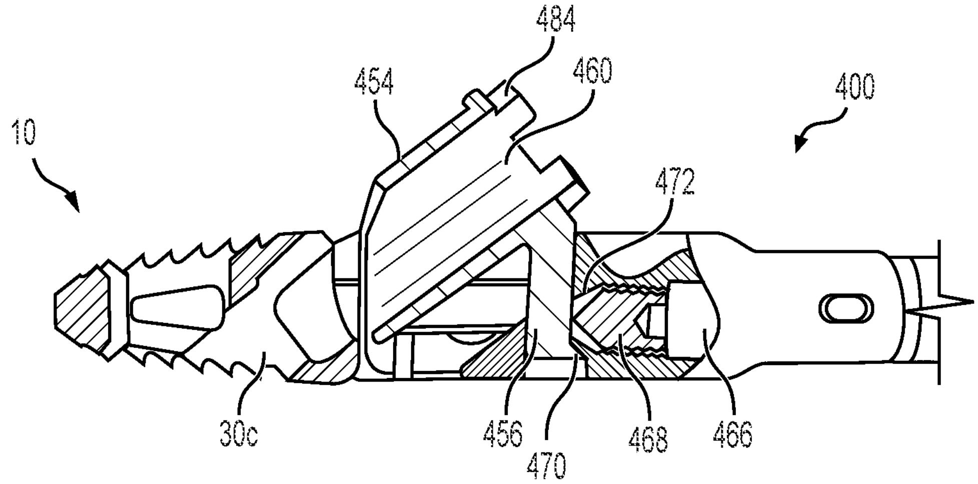
FIG. 21 shows a sectional view of a guide tube insertion instrument in association with an implant. The guide tube of the insertion instrument and the screw hole of the implant are aligned. The set screw is in the tightened position.
Figure 22:
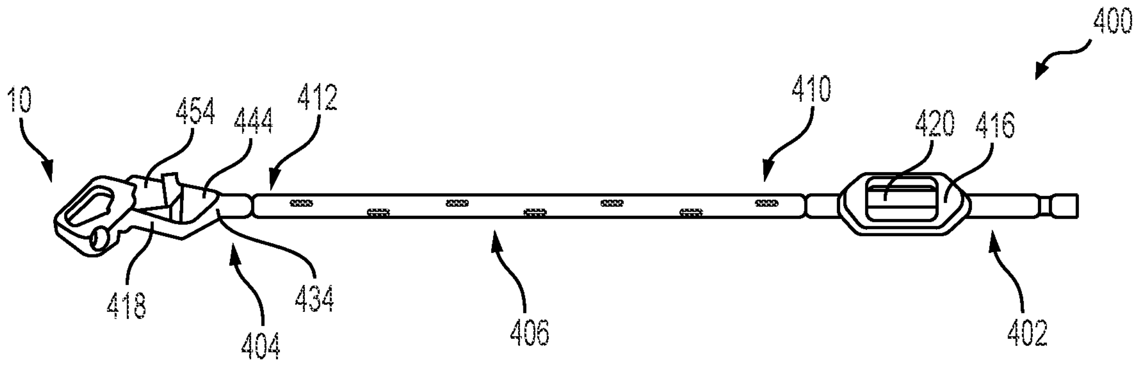
FIG. 22 shows a guide tube insertion instrument with an attached implant.

When the thumbwheel 420 is rotated, the internal draw rod 408 is translated in a distal direction and the lateral insertion arm rotates about the pivot point 452, resulting in the lateral arm moving to an open position as shown in FIG. 16A-C. When the thumbwheel 420 is rotated in the opposite direction, the internal draw rod 408 is translated proximally and the lateral insertion arm 426 rotates about the pivot point 452 to return to the closed position as shown in FIG. 17A-C. As shown in FIG. 17A, 17B, when the lateral insertion arm is in the closed position, the engagement prong 438 at the distal tip of the lateral engagement arm 426 engages the lateral engagement recess 34 on the implant 10 to secure the connection of the implant 10 to the insertion tool 400.

The insertion tool 400 also comprises an alignment guide tube 454. As shown in FIGS. 16-21, the guide tube 454 may be mounted on the insertion head 434 in a recess located between the insertion arms 418, 426. The insertion head 434 comprises a guide tube alignment aperture that passes through the insertion head 434 from the upper surface 444 to the lower surface 446. The insertion head 434 also comprises a set screw aperture 466 that extends into the insertion head in direction parallel to the upper 444 and lower 446 surfaces, and perpendicular to and intersecting the guide tube alignment aperture 458. The set screw aperture is threaded and is dimensioned to receive a threaded set screw 468 therein.

The guide tube 454 is generally cylindrical with a leading edge 488, a trailing edge 490, and a lumen 460. The trailing edge 490 of the guide tube 454 may include crenellations 484 that interlock with corresponding crenellations 640 on the driver 600 as described below. Alternatively, the trailing edge 490 of the guide tubes may end in an alternative geometric surface that may interact with the driver in a keyed mechanism. In some embodiments, the trailing edge of the guide tubes may end in a flat surface.

The guide tube 454 is fixedly attached to a guide tube post 456. The guide tube post 456 is dimensioned to pass through the guide tube alignment aperture 458 and allows the adjustment of the guide tube 456 in an upward or downward direction by sliding within the aperture 458. In some embodiments there is a small projection 470 at the base of the guide tube post 456 that will strike the lower edge of the tip 472 of the set screw 468 to prevent removal of the tube post 456 from the aperture 458. The set screw 468 engages the guide tube post 456 and prevents movement of the guide tube post 456 within the aperture 458.

Figure 27A:
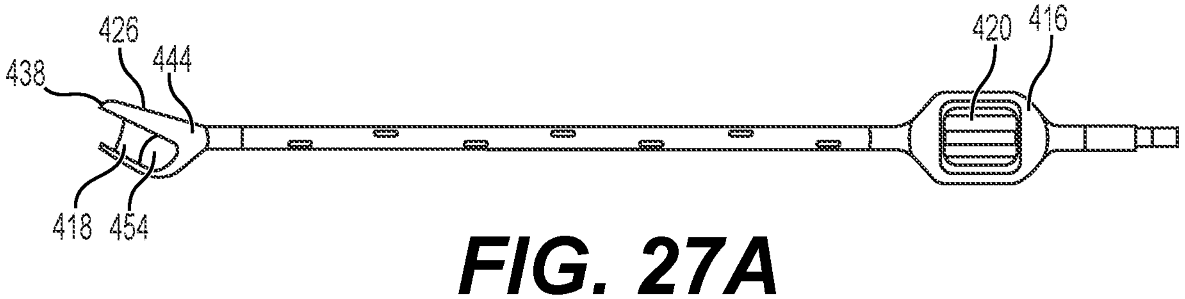
FIGS. 27A-27B show views of guide tube insertion instruments for left (FIG. 27A) and right (FIG. 27B) anterolateral approaches.
Figure 27B:
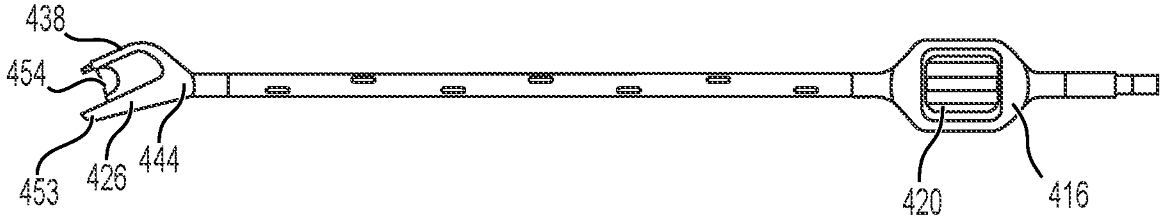

As shown in FIG. 27A-B, the insertion instrument may be utilized for either a left-side or right-side anterolateral approach depending upon the direction of the insertion head 434.

Figure 23:
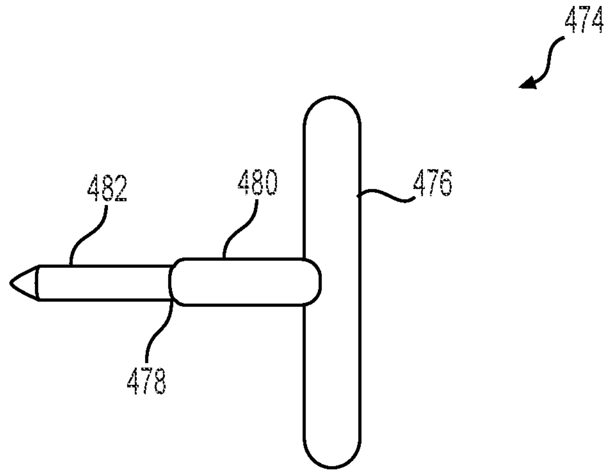
FIG. 23 shows an alignment tool.
Figure 24:
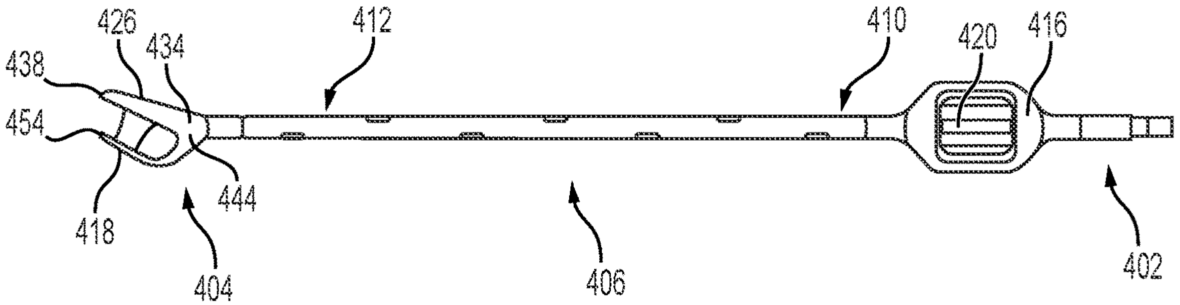
FIG. 24 shows a top view of the guide tube insertion instrument of FIG. 16.
Figure 25:
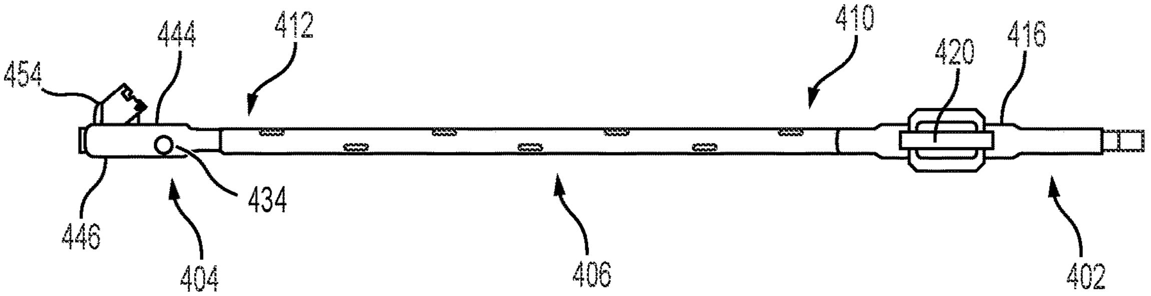
FIG. 25 shows a side view of the guide tube insertion instrument of FIG. 16.
Figure 26:
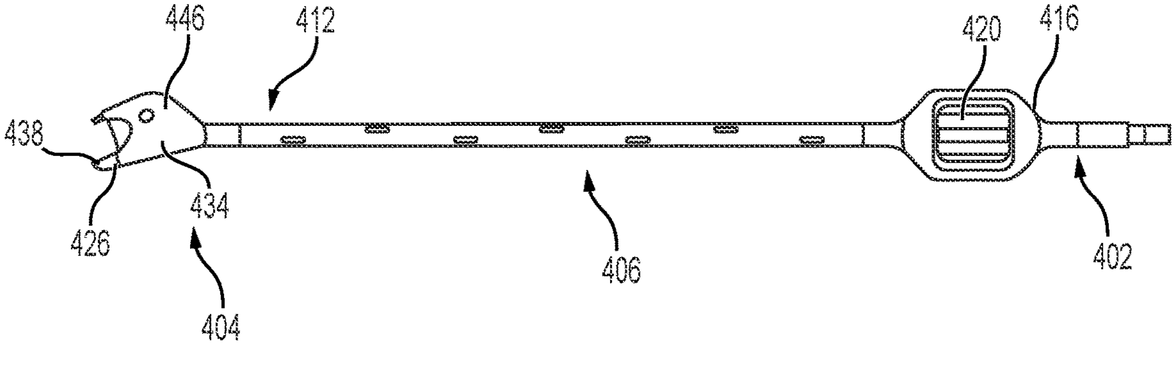
FIG. 26 shows a bottom view of the guide tube insertion instrument of FIG. 16.

According to one embodiment, the guide tube 454 is aligned with the screw hole 30 on the implant 10 through the use of an alignment tool 474 as shown in FIG. 23. The alignment tool 474 comprises a handle 476 and an alignment rod 478. As shown in FIG. 23, in some embodiments the alignment rod 478 may have a larger diameter 480 at the proximal end of the tool, sized for engaging the guide tube 454, and a smaller diameter 482 at the distal end, sized for engaging the screw hole 30.

To prepare the insertion device 400 for use in surgery, the thumbwheel 420 is rotated to translate the internal draw rod 408 distally and move the lateral insertion arm 426 to the open position. The medial insertion arm 418 is inserted into the medial insertion aperture 32 of the implant 10 and the thumbwheel 420 is rotated in the opposite direction to translate the internal draw rod 408 proximally and move the lateral insertion arm 426 to the closed position. The engagement prong 438 will interact with the lateral engagement recess 34 to secure the implant 10 to the insertion instrument 400. It is then necessary to align the guide tube 454 of the insertion instrument 400 with the medial screw hole 30*c* of the implant 10. The set screw 468 is loosened and the alignment rod 478 is passed into the lumen 460 of the guide tube 454 and then into the medial screw hole 30*c*. When the alignment rod 478 is passed through both the guide tube 454 and the screw hole 30*c*, the two elements are correctly aligned. The set screw 468 is tightened and the alignment tool 474 is removed. The implant 10 is prepared for use in the surgical procedure.

Although the exemplary embodiment of an anterolateral inserter described herein incorporates an integrated guide tube, in some embodiments it may be preferable to have a single insertion instrument that may be used for either a right or left approach. In such a case, the insertion instrument 400 will not have an attached guide tube. In this way, the upper 444 and lower 446 surfaces of the insertion head 434 will be unencumbered by any protrusions allowing easy reversal of the instrument. Further, it may be preferable that the insertion instrument 400 is compatible with implants of any width. Therefore, in some embodiments, the insertion instrument 400 has two fixed arms that interact with the medial insertion apertures on an interbody implant. In this way, the pivoting lateral insertion arm 426 does not restrict the interbody implant 10 to a specific width, and a single inserter may be used for the insertion of implants of different sizes at different levels if necessary.

The insertion instruments described herein may be utilized to place an interbody implant between vertebral bodies. The guides disclosed herein will provide an ideal trajectory for placement of the screws to secure the implant in place. The screws may be placed by a driver which screws the anchor portion of the bone screw into the vertebral body. The driver also contains an internal hexabit driver for placement of set screws. However, one of the issues with placement of screws is that it is often difficult for the surgeon to know that screws are fully seated which leads to screws left proud, or screws stripped in bone. Previous methods to identify proper seating of screws have used saw teeth on guides to provide a hard stop. However, such devices do not provide visual or audible indication, and the tactile stop is limited to when the teeth come into contact. Another method that has been used is blasting the surfaces of screws and plates to introduce roughness and provide some tactile feel when the roughened surfaces are in contact. However, this method does not include hard stop or visual or audible alert.

Disclosed herein is a visual, audio, and touch (VAT) mechanism integrated into the body of a driver that provides feedback to the surgeon when the screw is properly set. Use of a visual, audio and touch mechanism ensures the screw is fully seated, but not over tightened.

Figure 28:
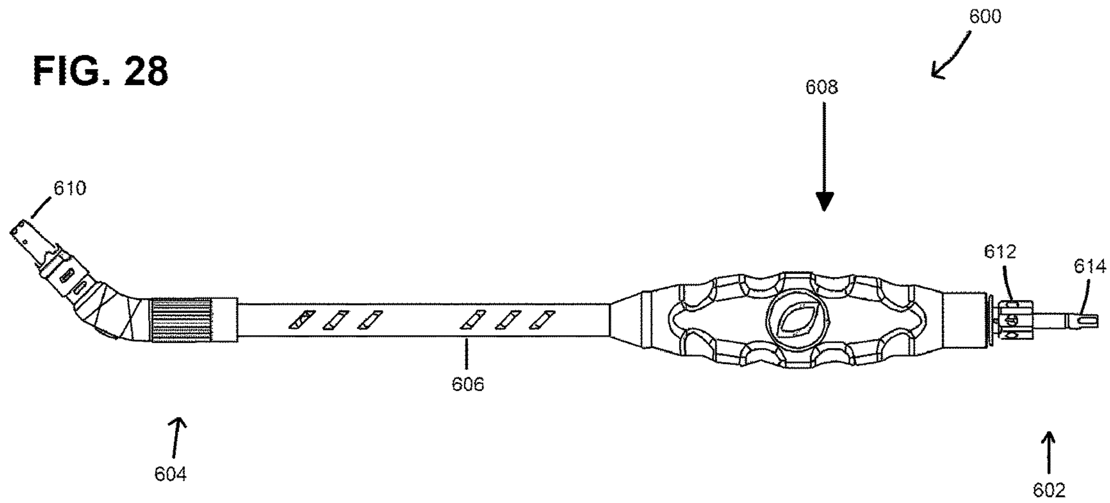
FIG. 28 shows a VAT driver assembly according to one embodiment.

As shown in FIG. 28, an otherwise standard driver may incorporate any or all of the visual, audio, or touch mechanisms disclosed herein.

According to a broad aspect, the driver 600 has a proximal end 602, a distal end 604, and a central shaft 606. A handle 608 is located at the proximal end 602. A driver tip 610 and a hexabit driver 616 are located at the distal end 604. The proximal end further comprises a first rotation grip 612 for the driver tip 610, and a second rotation grip 614 for the hexabit driver 616. Each of the feedback mechanisms described herein is incorporated into the distal end of the driver as will be described more fully below. It will be understood that the present disclosure is described in relation to an angled driver. However, the features may be incorporated into a driver of any suitable shape. Such variations are encompassed by this disclosure and are within the skills of a person of ordinary skill.

Figure 29:
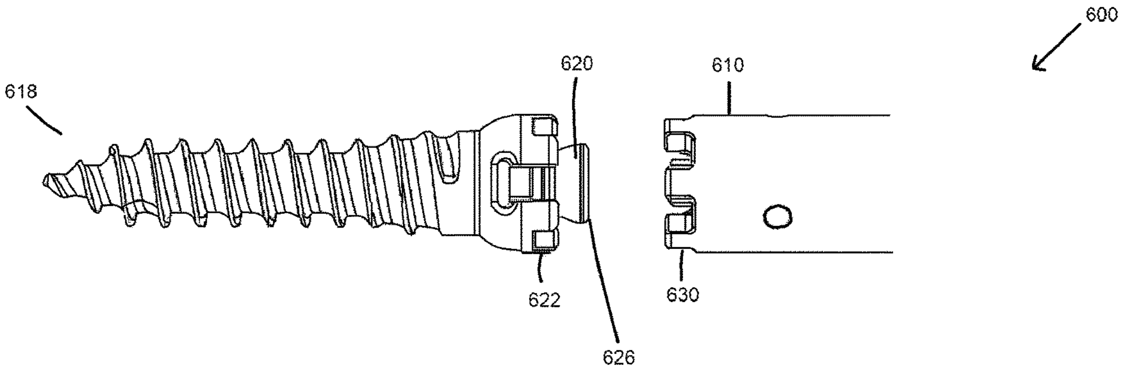
FIG. 29 shows a side view of the engagement between a bone screw and the driver tip.
Figure 30:
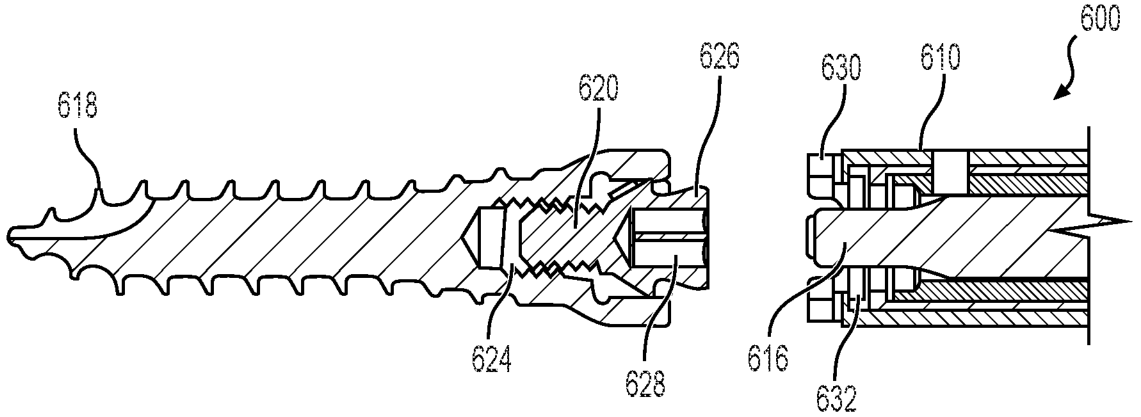
FIG. 30 shows a sectional view of the engagement between a bone screw and driver tip.
Figure 31:
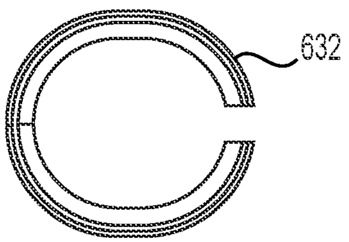
FIG. 31 shows a view of the c-clip.

FIGS. 29 and 30 show a detailed view and sectional view of the bone screw 618, bone anchor set screw 620, and the driver tip 610. The bone screw 620 has a crenellated head 622 and a threaded recess 624 to receive the set screw 620. As shown in FIG. 30, the set screw 620 has a hex recess 628 and a tapered head 626 that is dimensioned to fit inside the driver tip 610. The driver 600 has crenellations 630 at the driver tip 610 wherein the crenellations are complementary to the crenellated head 622 of the bone screw 620. When properly aligned, the crenellations are interdigitated and secure the connection between the driver 600 and bone screw 618. This secure connection translates the torsional force from the rotation of the first rotation grip to drive the bone screw 618 into the vertebral body. The driver 600 also comprises a hexabit driver 616 as shown in FIG. 30. The hexabit driver 616 interlocks with the hex recess 628 of the set screw 620. The rotation of the second rotation grip 614 drives the threaded set screw 620 into the threaded recess 624 of the bone screw 618. The c-clip 632 shown in FIGS. 30 and 31 functions to grip the set screw head 626 to stabilize the connection between the set screw 620 and the driver 600. The oblong shape of the c-clip 632, retains the clip centered in the driver 600 while ensuring engagement with the set screw heads 626 on the narrow sides.

Figure 32:
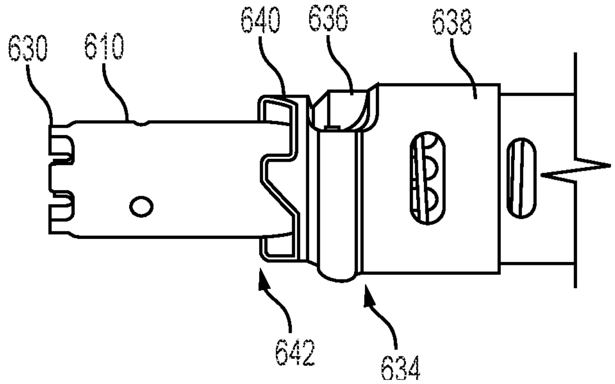
FIG. 32 shows a view of the driver tip with the VAT mechanism.
Figure 33:
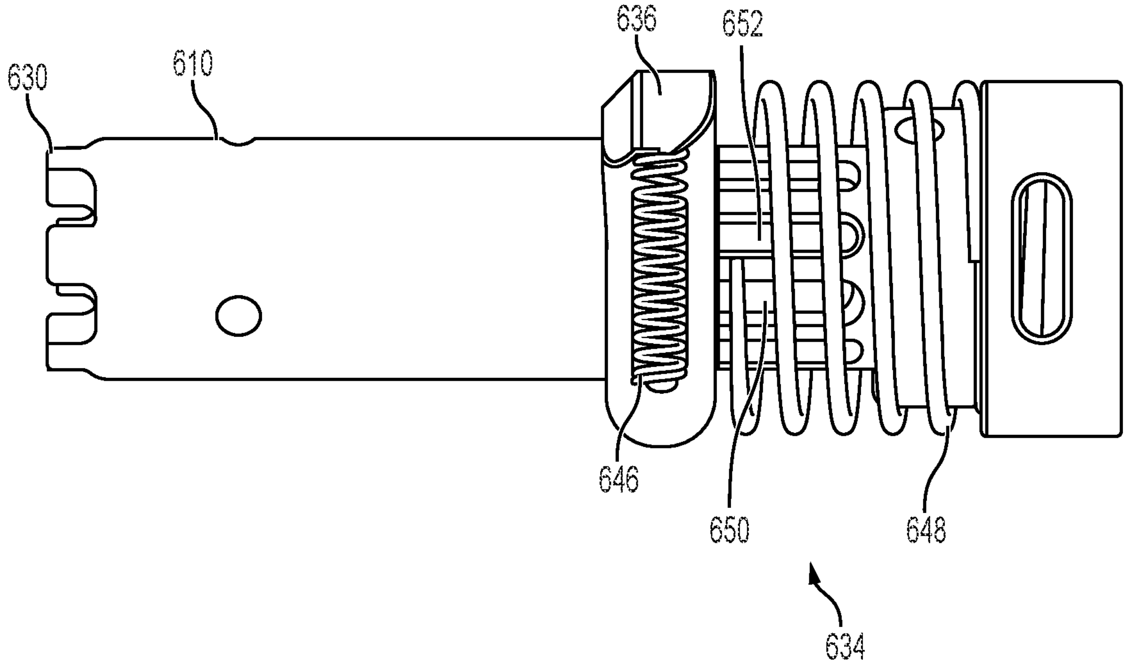
FIG. 33 shows a view of the driver tip with the VAT mechanism, where the VAT sleeve has been removed to show the detail beneath.
Figure 34:
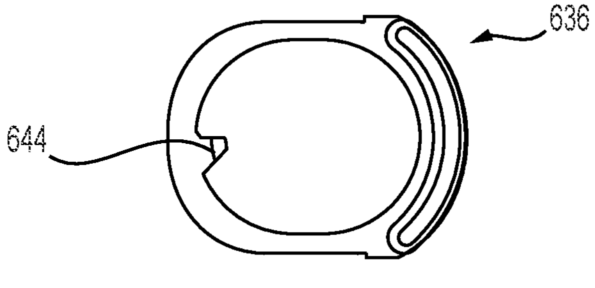
FIG. 34 shows a view of the VAT button.

In one exemplary embodiment, the driver further comprises an indicator that the screw is properly seated. The indicator may be a visual, audio, and touch (VAT) mechanism 634 that provides feedback to the surgeon when the screw is properly set. As shown in an exemplary embodiment in FIG. 32, the VAT mechanism 634 comprises a button 636, a sleeve 638, and VAT crenellations 640. The VAT sleeve 638 is rotatable and translatable about the driver 600. The VAT button 636 is contained in the VAT sleeve 638 and rotates and translates with the sleeve 638. The distal end 642 of the VAT sleeve 638 terminates in the VAT crenellations 640.

Figure 35:
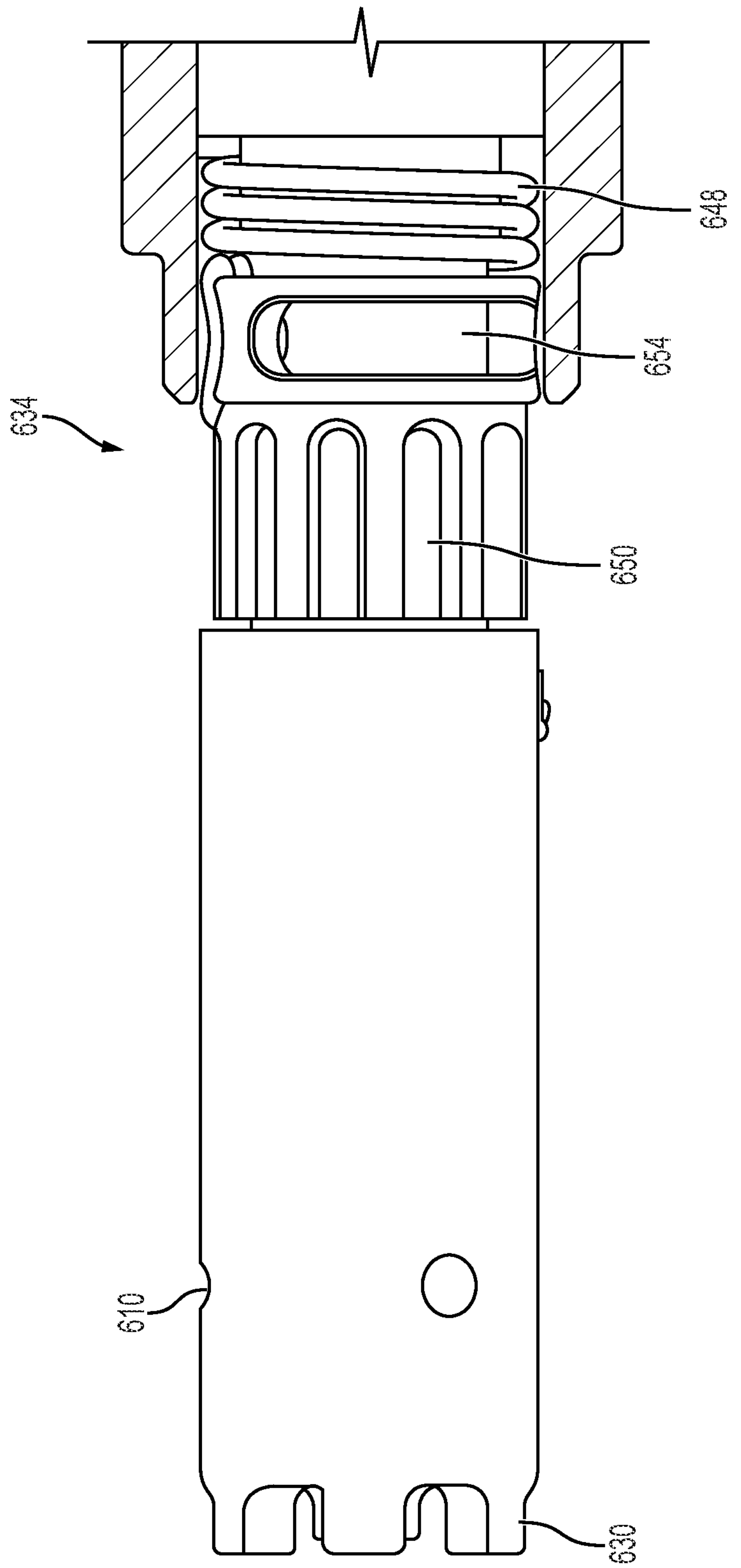
FIG. 35 shows a view of the driver tip including the VAT mechanism, where the VAT sleeve has been removed. The VAT spring is compressed as when the bone screw is fully seated.

FIG. 35 shows the VAT mechanism 634 with the VAT sleeve 638 removed. As shown, beneath the VAT sleeve 638 is the VAT sleeve spring 648 which encircles the internal splines 650 of the VAT mechanism. The VAT sleeve spring 648 forces the sleeve 638 distally relative to the driver 600. As the bone screw 618 is driven into the vertebral body, the VAT sleeve spring 648 will be compressed and the sleeve 638 will translate proximally relative to the driver 600. Beneath the VAT sleeve spring 648 is the internal spline 650 comprising a plurality of longitudinal grooves 652 arranged around the circumference of the driver 600. The spline 650 is held in place by a spline pin 656. The spline 650 also has an internal slot 654, as shown in FIG. 35. The spline pin 656 can translate through the slot 654 which allows the spline 650 to rotate the length of the slot 654.

The VAT button 636 further comprises a button spring 646 and a button tooth 644. The button spring forces the VAT button 636 outward. The VAT button 636 rests on the driver 600 when the VAT sleeve 638 is in the distal position. The insertion of the screw results in compression of the sleeve spring 648 and proximal translation of the VAT sleeve, until the button tooth 644 engages the spline.

Figure 36:
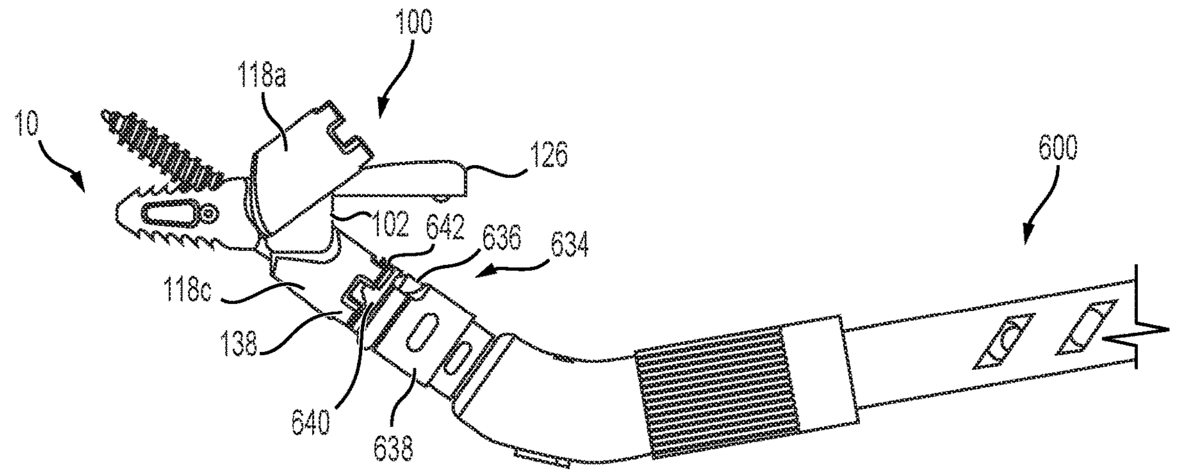
FIG. 36 shows a detail view of the VAT driver assembly which includes the driver of FIG. 28 engaged with the 3-hole guide of FIG. 2 and the implant of FIG. 1.
Figure 37:
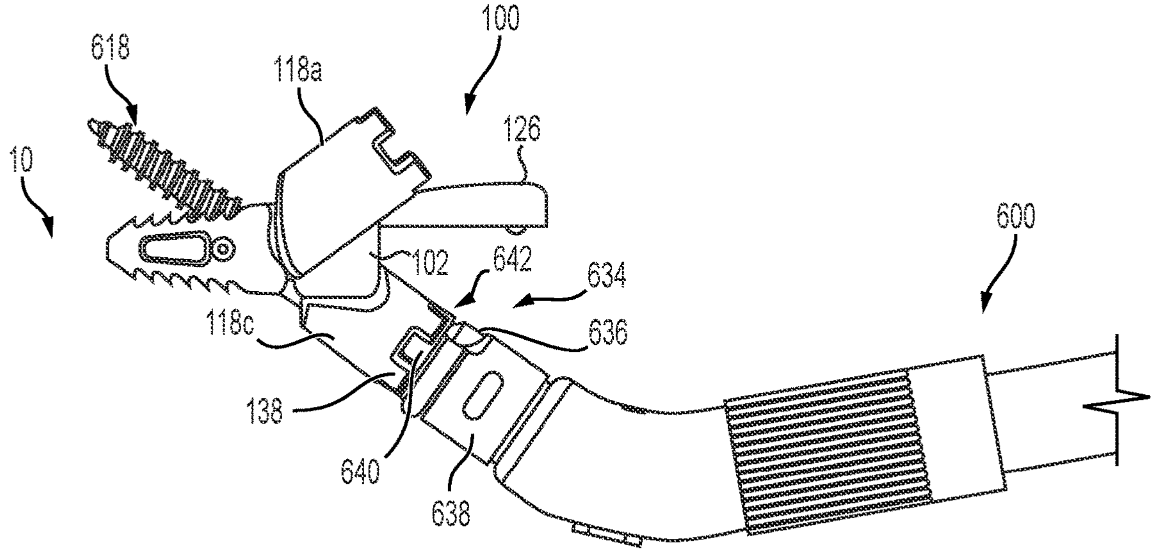
FIG. 37 shows the VAT driver assembly of FIG. 36 where the VAT sleeve has been translated proximally relative to the driver due to insertion of the screw.
Figure 38:
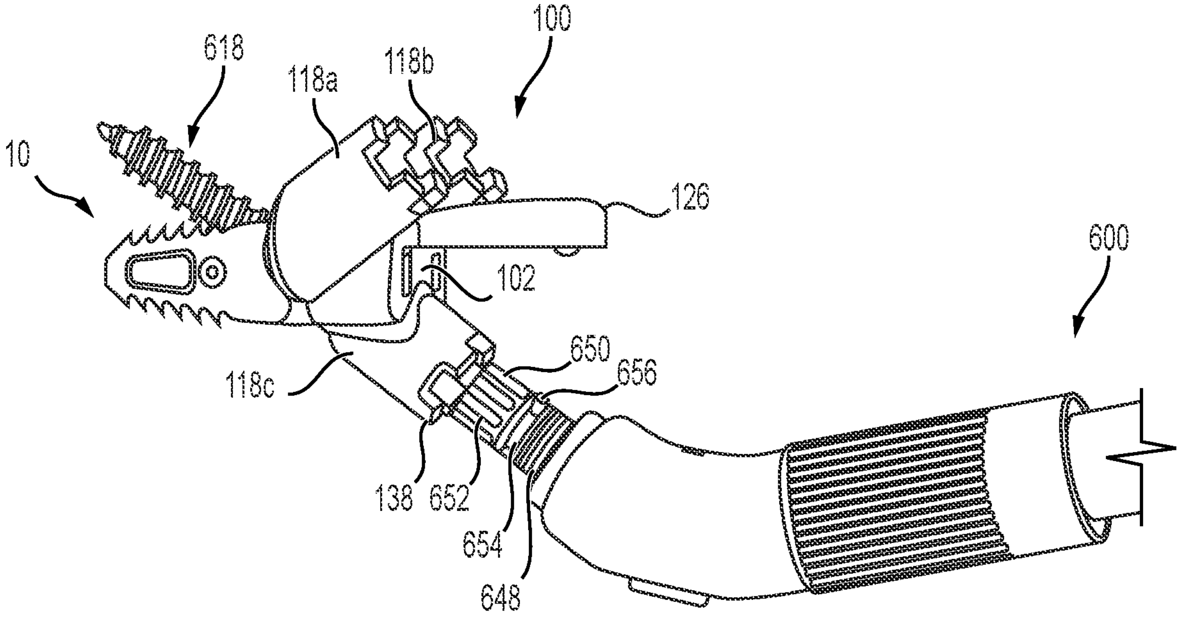
FIG. 38 shows the VAT driver assembly of FIG. 36 where the VAT sleeve has been removed to show the position of the VAT mechanism when the screw is fully seated.

FIGS. 36-38 show the driver 600 in use with a 3-tube guide as described above. Screw placement begins with the insertion of an interbody between intervertebral discs. As shown in FIG. 36, the insertion guides and insertion instrument with guides described herein may be use. The bone screw 618 with set screw 620 are affixed to the distal end 604 of the driver 600 and are held in place by the c-clip 632 which engages the head of the set screw 626. The driver 600 and bone screw 618 are inserted through the guide tube 118 and through the screw hole 30 of the interbody implant 10 to the location where the bone screw 618 will be inserted.

Figure 2:
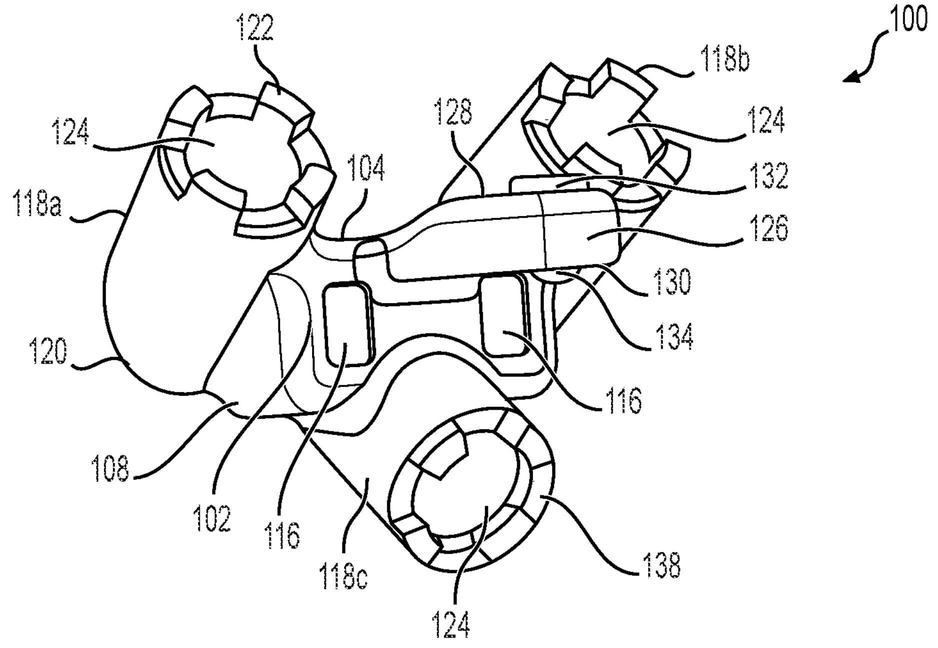
FIG. 2 shows a rear perspective view of a 3-hole guide according to an exemplary embodiment.
Figure 3:
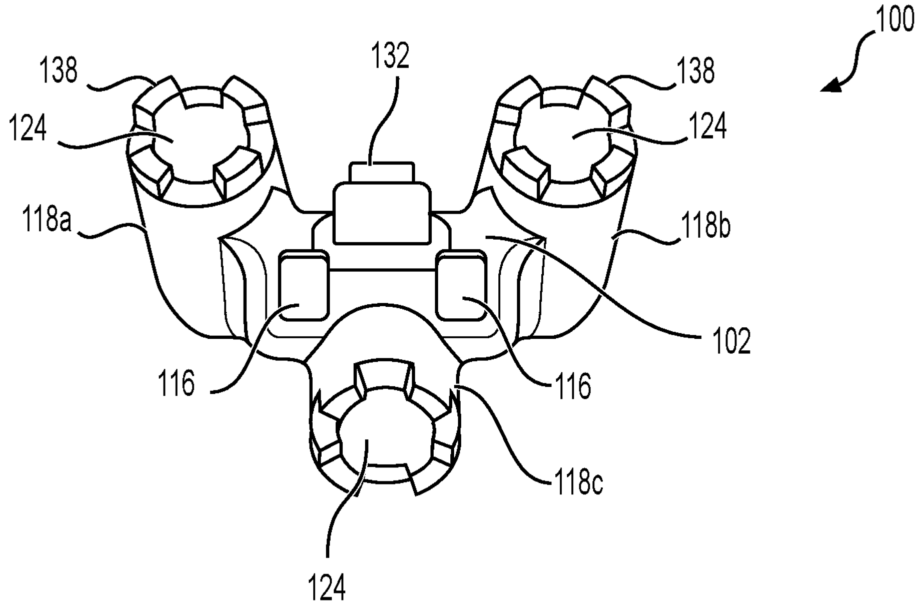
FIG. 3 shows a rear view of the guide of FIG. 2.
Figure 4:
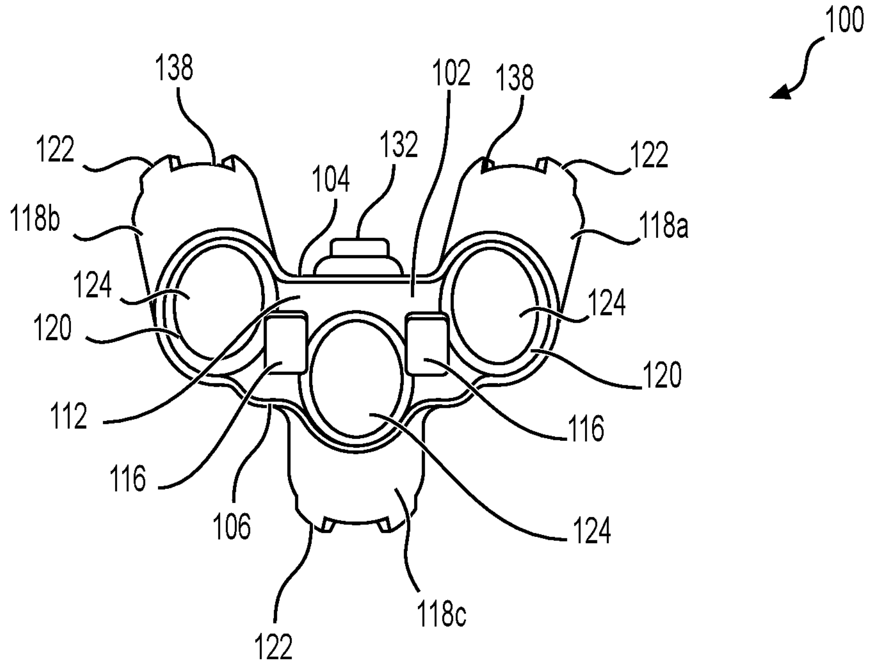
FIG. 4 shows a front view of the guide of FIG. 2.
Figure 5:
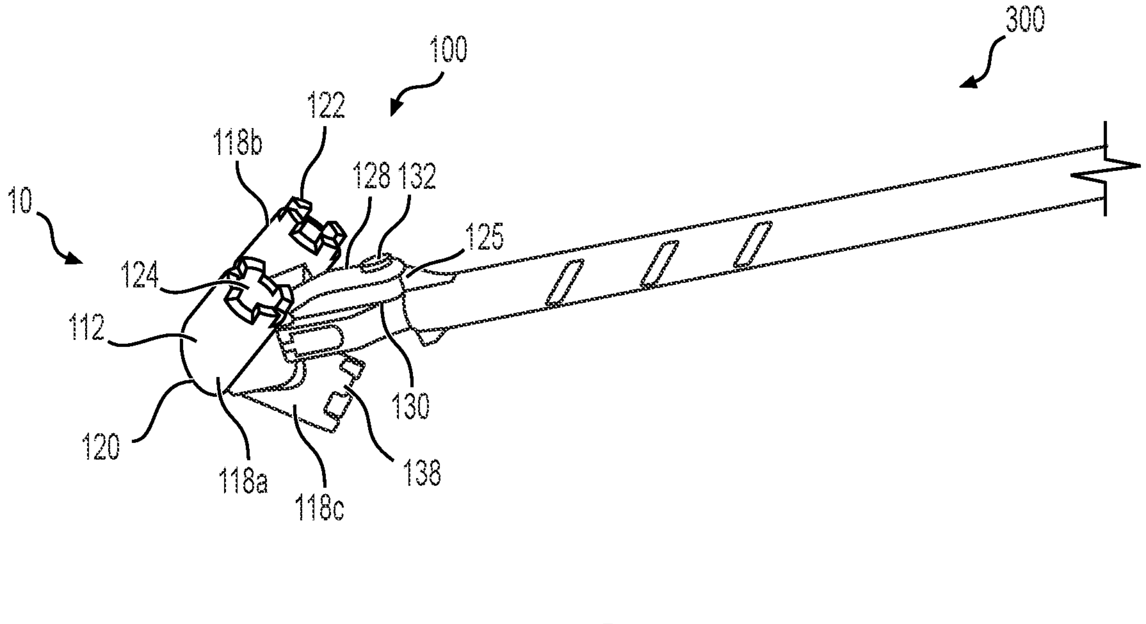
FIG. 5 shows an insertion assembly comprising an implant, 3-hole guide, and insertion instrument according to an exemplary embodiment.
Figure 6:
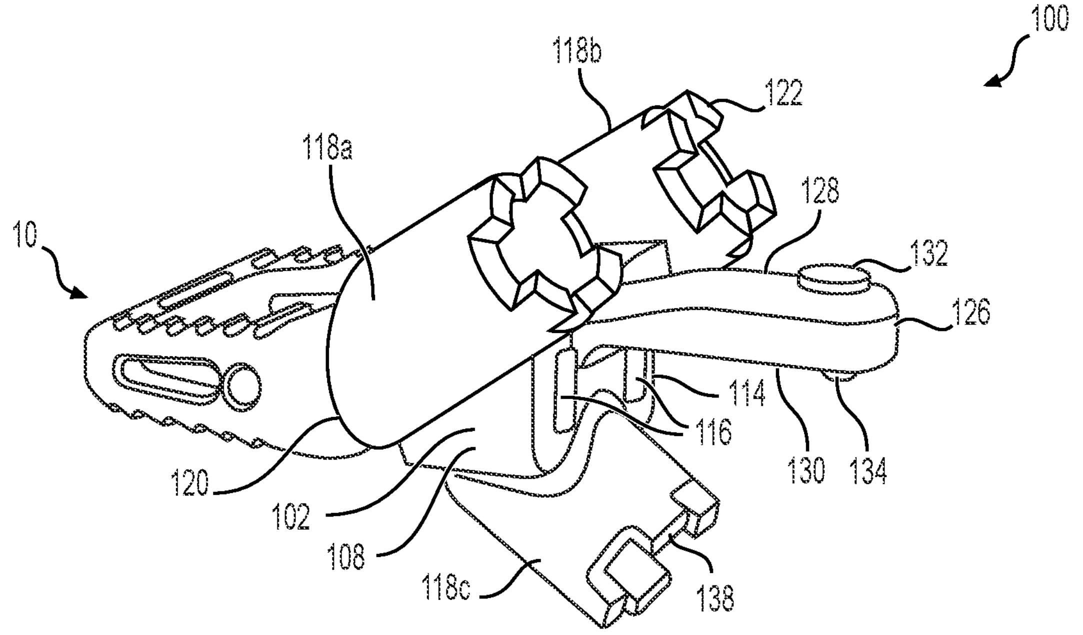
FIG. 6 shows a side perspective view of the guide of FIG. 2 in combination with the implant of FIG. 1.
Figure 7:
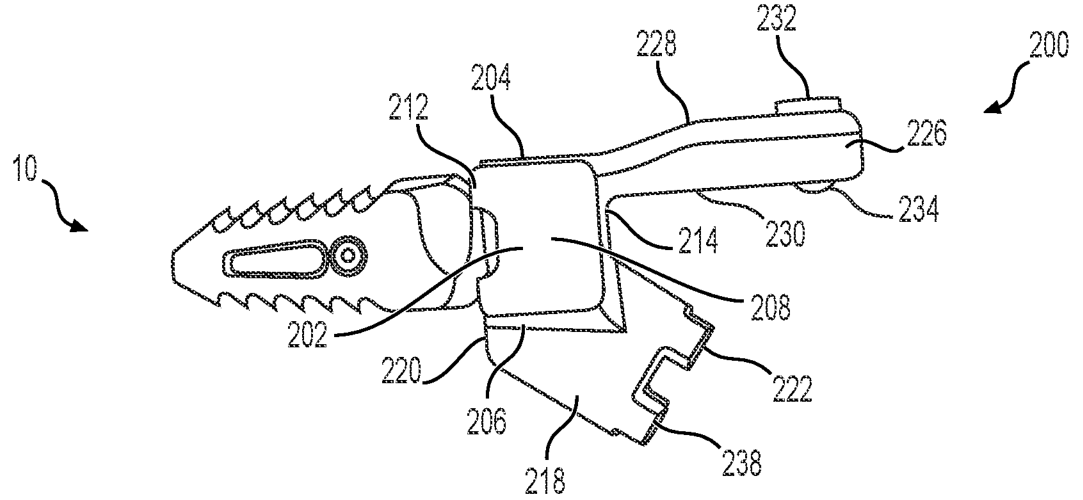
FIG. 7 shows a side view of the implant of FIG. 1 in combination with a 1-hole guide.
Figure 8:
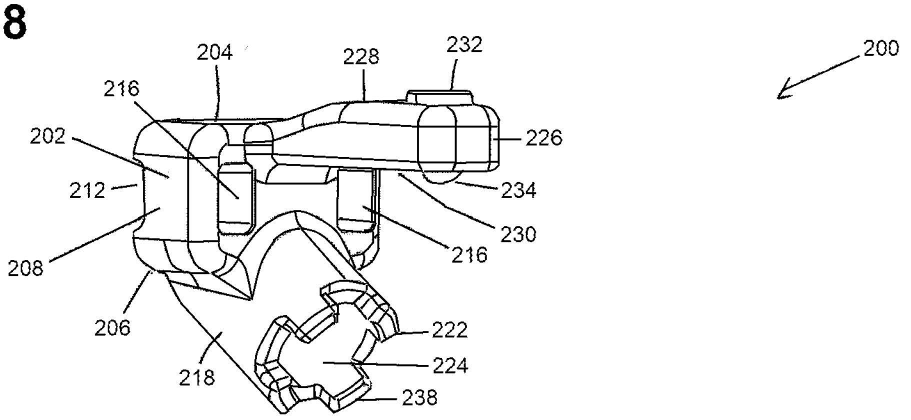
FIG. 8 shows a side perspective of the 1-hole guide of FIG. 7.
Figure 9:
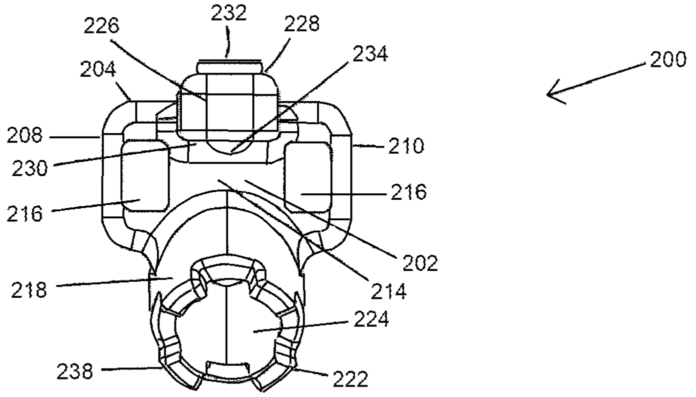
FIG. 9 shows a rear view of the guide of FIG. 7.
Figure 10:
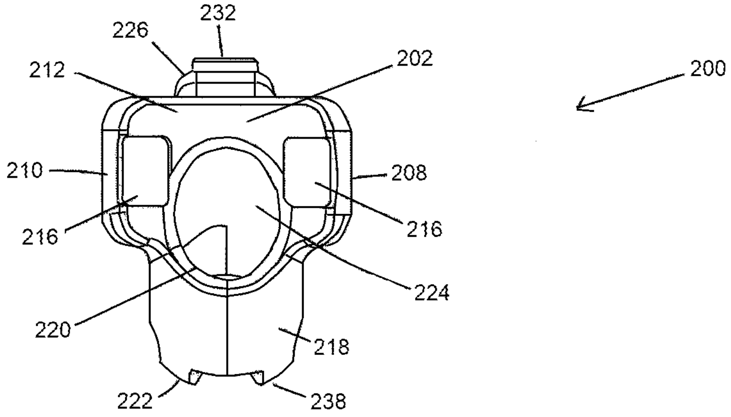
FIG. 10 shows a front view of the guide of FIG. 7.
Figure 11:
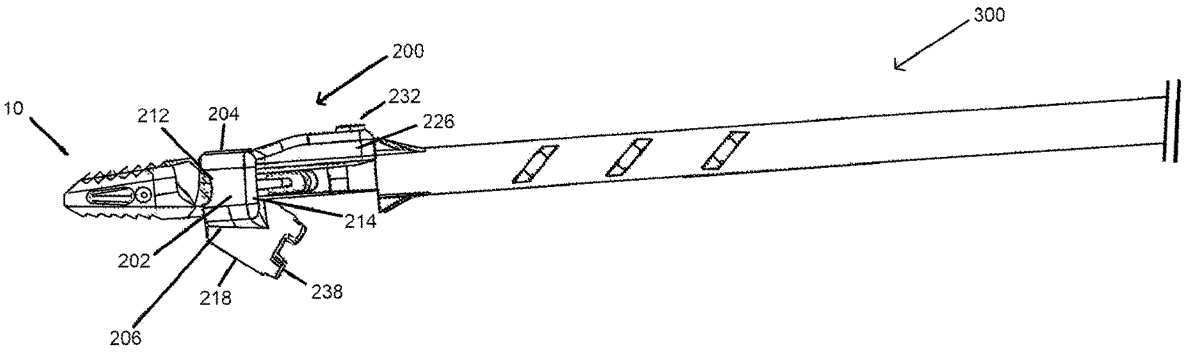
FIG. 11 shows an insertion assembly comprising an implant, 1-hole guide, and insertion instrument according to an exemplary embodiment.
Figure 12:
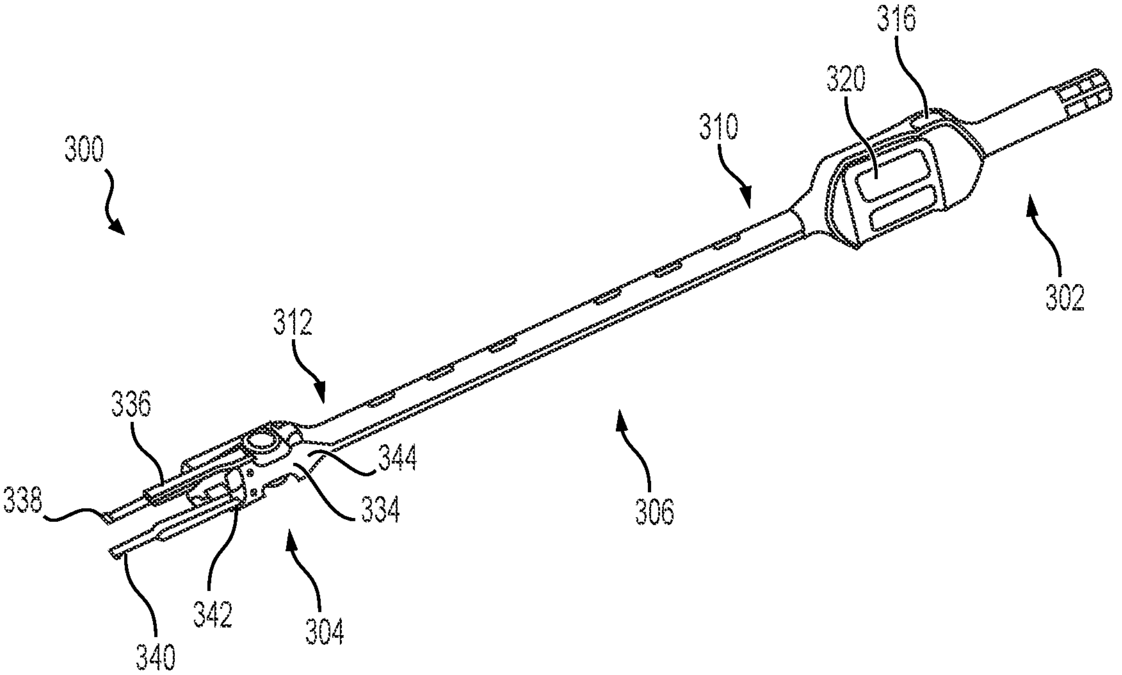
FIG. 12 shows a perspective view of an inserter according to one embodiment.
Figure 13:
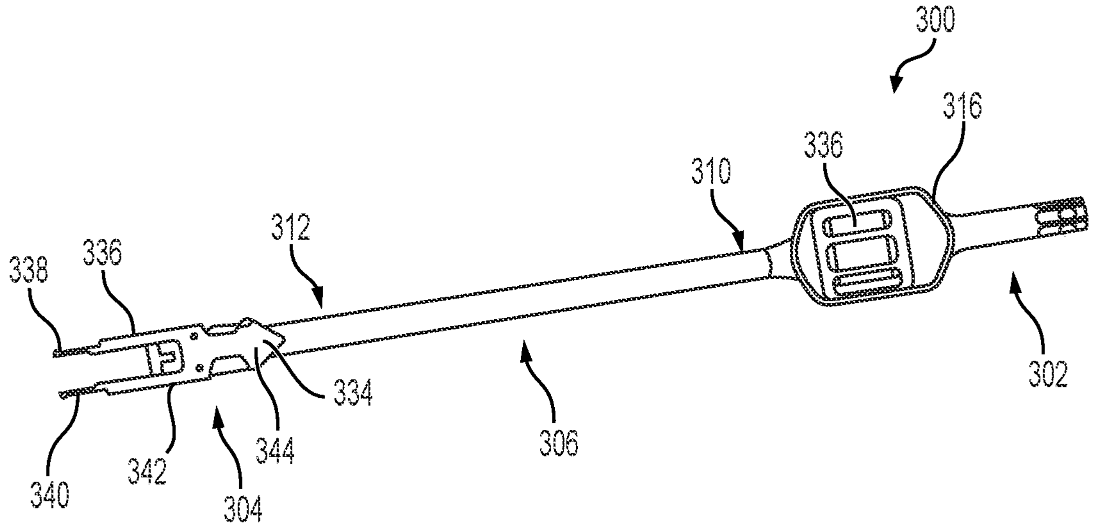
FIG. 13 shows a bottom view of the inserter of FIG. 12.

The guide tubes 118 described herein have crenellations on the trailing edge 222 of the tubes (as shown for example in FIGS. 2 and 16). The guide tube crenellations 138 are complementary to the VAT crenellations 640 such that proper alignment of the guide tube 118 and VAT driver 600 will lead to the interdigitation of the crenellations. When the VAT driver 600 is seated with the guide tube 118 prior to insertion of the screw, the VAT sleeve 638 is in the distal position as shown in FIG. 36. The first rotation grip 612 is rotated to drive the screw 618 distally into the vertebral body. Because the guide tube crenellations 138 and the VAT crenellations 640 maintain the guide tube 118 and VAT sleeve 638 in a fixed position relative to one another, translation of the bone screw 618 in the distal direction results in compression of the sleeve spring 648 and proximal translation of the VAT sleeve 638 relative to the driver, as shown in FIG. 37.

The VAT mechanism 634 provides three indicators to the surgeon that the bone screw 618 is properly seated. When the screw 618 is sufficiently translated so that it interacts with the spherical surface 38 of the screw hole 30 of the implant 10, the VAT button 636 which translates proximally with the VAT sleeve 638, reaches the spline 650. The tension on the button spring 646 will cause the VAT button 636 to pop out providing both an audible and visual indicator that the bone screw 618 is properly seated. Additionally, when the VAT button 636 pops out, the button tooth 644 will engage the spline 650. The spline 650 can rotate against the sleeve spring 648 until the end of the spline slot 654 reaches the spline pin 656. When the spline pin 656 reaches the end of the spline slot 654, the spline 650 prevents the driver from further rotation to drive the screw, resulting in a hard tactile stop. The tactile alert of the hard stop is regulated by the length of the spline slot 654. Thus the delay between button tooth engagement and hard stop may be increased or decreased by adjusting the length of the spline slot 654. Such variation can ensure full engagement of teeth, and provide a delayed response if desired to accommodate tolerance stack.

The VAT mechanism 634 as described in this exemplary embodiment provides visual and audible indications that the screw is properly set in the form of the VAT button popping out, and a tactile indication in the form of a hard stop when rotation will no longer occur. Once these indicators are received, the surgeon will rotate the second rotation grip to place the set screw 620. While the embodiment described herein encompasses visible, audible, and tactile indicators that a screw is fully set, other embodiments may involve any visible, audible, or tactile indicators, alone or in combination. For example, one embodiment may comprise the hard stop of the spline, but without the visual and audible indicator of the button. Alternatively, another embodiment may comprise the button to provide a visual and audible indication, but without the tactile component of a hard stop.

While the embodiments described herein have interlocking crenellations on the guide 100 and driver 600, alternative interlocking mechanisms may be used. In one alternative embodiment, the sleeve 638 and trailing edge of the guide tube 122 have a keyed interlocking mechanism to secure the connection during installation of the screws 618. The pattern may be of any form, so long as the patterns of the sleeve 638 and guide tube 122 are complementary. In other embodiments, the sleeve 638 and trailing edge of the guide tube 122 may be smooth and without interlocking features at all. In such embodiments, the interaction between the crenellated driver tip 610 and the crenellated bone screw 618 stabilizes the connection between the driver 600 and guide 100.

Additionally, alternative visual indicators may be used. Further, while the exemplary embodiment described has a VAT mechanism 634 contained within a translatable sleeve 638, other mechanisms are possible which do not require the bulk of a sleeve 638 external to the driver 600.

Figure 39:
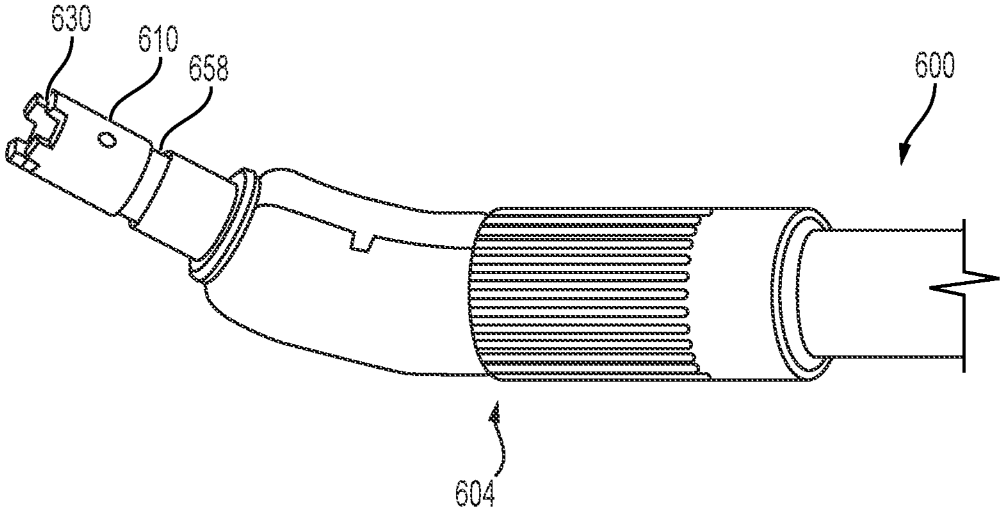
FIG. 39 shows an alternative embodiment of a driver with a visual indicator that the screw is fully seated.

For example, the embodiment shown in FIG. 39 comprises a colored band as a visual indicator. In this exemplary embodiment, the driver tip 610 is translatable relative to the body of the driver 600. A colored band 658 is proximal to the driver tip 610 and the outer diameter of the colored band 658 is smaller than the inner diameter of the driver tip 610. As the bone screw 618 is inserted, the outer tip 610 translates proximally relative to the driver 600 and the colored band 658 is covered by the driver tip 638. When the colored band 658 is no longer visible, the bone screw 618 is properly seated and the set screw 620 may be placed.

While the exemplary embodiment includes a guide between the screw driver and the interbody device (the ultimate destination of the screw) it is further contemplated that the interbody may have a direct interaction with the VAT mechanism in instances when there is no intermediate guide structure between the interbody or plate and the screw driver. In some embodiments, crenellations could be manufactured into the interbody or plate to provide an interlocking surface for engagement of the interbody and the VAT mechanism.

Other combinations of visual, audible, and tactile indicators are possible and are within the scope of this disclosure. The indicators may be components of an external sleeve, or may be internal components which allow translation of the driver tip. Such variations are within the knowledge an ability of one in the skill in the art.

What is claimed is:

1. A driver for implanting a bone screw into a bone through an interbody implant, the driver comprising:

a shaft extending between a distal end and a proximal end;

a handle coupled to the shaft at the proximal end; and a visual, audio, and touch (VAT) mechanism positioned between the proximal end and the distal end of the shaft, wherein the VAT mechanism is configured to provide an audible, visual and tactile indicators when the bone screw engages the interbody implant wherein the VAT mechanism comprises:

a sleeve configured to rotate about the shaft and to translate between the proximal end and the distal end;

a button;

a button spring configured to bias the button radially outward relative to the shaft; and a button tooth configured to be engaged in response to proximal translation of the sleeve.

2. The driver of claim 1, wherein the VAT mechanism provides the audible, visual and tactile indicators when a head of the bone screw engages a surface of the interbody implant.

3. The driver of claim 1, wherein the VAT mechanism provides the audible, visual and tactile indicators when a head of the bone screw engages a spherical surface of the interbody implant.

4. The driver of claim 1, wherein the VAT mechanism further comprises a sleeve spring configured to compress and translate the sleeve proximally in response to driving the bone screw into the bone.

5. The driver of claim 4, wherein the sleeve spring is configured to bias the sleeve toward the distal end.

6. The driver of claim 1, wherein the button is configured to provide the audible and visual indicators in response to implanting the bone screw.

7. The driver of claim 6, wherein the audible and visual indicators include the button extending through an aperture in the sleeve in response to proximal translation of the sleeve.

8. The driver of claim 1, further comprising:

a driver tip at the distal end of the shaft, the driver tip being configured to engage the bone screw;

a set screw driver disposed within the driver tip and configured to engage a set screw disposed within the bone screw; and a first rotational grip and a second rotational grip disposed at the proximal end of the shaft, wherein the first rotational grip is configured to rotate the driver tip and the second rotational grip is configured to rotate the set screw driver.

9. The driver of claim 8, wherein the driver tip comprises a crenellation configured to engage a complementary crenellated head of the bone screw.

10. The driver of claim 8, wherein the set screw driver comprises a hexabit driver configured to engage a hex recess of the set screw.

11. The driver of claim 8, further comprising a clip disposed within the driver tip and configured to engage a head of the set screw, wherein the clip is configured to stabilize engagement between the set screw driver and the set screw.

12. The driver of claim 8, wherein the first rotational grip is configured to rotate and to drive the bone screw into the bone.

13. The driver of claim 8, wherein the second rotational grip is configured to rotate and to drive the set screw into a threaded recess of the bone screw.

14. A system for implantation of an interbody implant comprising the driver of claim 1 and the bone screw.

15. A system for implanting an interbody implant between adjacent vertebral bodies, comprising:

an interbody implant configured to be positioned between adjacent vertebral bodies;

a bone screw configured to secure the interbody implant to a bone of adjacent vertebral bodies;

an insertion instrument for providing a trajectory for placement of the bone screw during implantation of the interbody implant; and a driver configured to drive the bone screw into the bone and provide feedback to a user during implantation, the driver including:

a shaft extending between a distal end and a proximal end;

a handle coupled to the shaft at the proximal end; and a visual, audio, and touch (VAT) mechanism positioned between the proximal end and the distal end of the shaft, wherein the VAT mechanism is configured to provide audible, visual and tactile indicators when the bone screw engages the interbody implant;

wherein the VAT mechanism comprises:

a sleeve configured to rotate about the shaft and to translate between the proximal end and the distal end;

a button;

a button spring configured to bias the button radially outward relative to the shaft; and a button tooth configured to be engaged in response to proximal translation of the sleeve.

16. The system of claim 15, wherein the VAT mechanism provides the audible, visual and tactile indicators when a head of the bone screw engages a surface of the interbody implant.

17. The system of claim 15, wherein the VAT mechanism provides the audible, visual and tactile indicators when a head of the bone screw engages a spherical surface of the interbody implant.

18. The system of claim 15, wherein the VAT mechanism further comprises a sleeve spring configured to compress and translate the sleeve proximally in response to driving the bone screw into the bone.

* * * * *